United States Patent [19]

Moriwaki et al.

[11] Patent Number: 4,937,240
[45] Date of Patent: Jun. 26, 1990

[54] THIENOTRIAZOLODIAZEPINE COMPOUNDS AND PHARMACEUTICAL USES THEREOF

[75] Inventors: Minoru Moriwaki, Oita; Hiroshi Tanaka, Fukuoka; Michio Terasawa; Tetsuya Tahara, both of Oita, all of Japan

[73] Assignee: Yoshitomi Pharmaceutical Industries, Ltd., Osaka, Japan

[21] Appl. No.: 302,874

[22] Filed: Jan. 30, 1989

[30] Foreign Application Priority Data

Jan. 30, 1988 [JP] Japan .................. 63-20400
Apr. 26, 1988 [JP] Japan .................. 63-103221
Dec. 6, 1988 [JP] Japan .................. 63-308365
Dec. 8, 1988 [JP] Japan .................. 63-311688

[51] Int. Cl.$^5$ .............. C07D 413/12; C07D 417/12; A61K 31/42; A61K 31/425
[52] U.S. Cl. ..................... 514/212; 514/220; 540/524; 540/565
[58] Field of Search ............. 540/565, 524; 514/220, 514/212; 546/192

[56] References Cited

U.S. PATENT DOCUMENTS 4,621,083 11/1988 Casels-Stenzel et al. ........... 514/220

FOREIGN PATENT DOCUMENTS 0194416 9/1980 European Pat. Off. .
0230942 8/1987 European Pat. Off. .
0240899 10/1987 European Pat. Off. .
0254245 1/1988 European Pat. Off. .

OTHER PUBLICATIONS

Weber et al., Chemical Abstracts, vol. 106, 1987, 156502h.
Stransky et al., Chemical Abstracts, vol. 107, 1987, 198366t.
Casels-Stanzel et al., J. of Pharmacology and Experimental Therapeutics, vol. 24, 3, 1987, 974 to 981.
Japanese Journal of Pharmacology, vol. 44, pp. 381-391.

Primary Examiner—Mukund J. Shah
Assistant Examiner—E. C. Ward
Attorney, Agent, or Firm—Sughrue, Mion, Zinn, Macpeak & Seas

[57] ABSTRACT

A thienotriazolodiazepine compound of the formula:

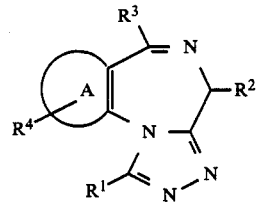

wherein each symbol is as defined in the specification or a pharmaceutically acceptable salt thereof, and pharmaceutical uses thereof.

Said compounds exhibit PAF-antagonistic activity and are useful for the prevention or treatment of various PAF-induced diseases.

3 Claims, No Drawings

THIENOTRIAZOLODIAZEPINE COMPOUNDS AND PHARMACEUTICAL USES THEREOF

BACKGROUND OF THE INVENTION

Benveniste et al. found a factor which strongly induced platelet aggregation from rabbit basophils, and named as platelet-activating factor (hereinunder referred to as PAF) in 1972. Hanahan et al. identified that the factor was phosphoglyceride of alkyl ether type having acetyl group in the 2-position, i.e. 1-o-hexadecyl or octadecyl-2-acetyl-sn-glyceryl-3-phosphorylcholine, in 1980.

The physiological roles of PAF have been intensively investigated, and it has been known that PAF was an important factor of various physiological reactions inclusive of platelet aggregation, reduction in blood pressure, immediate allergic reaction, contraction of smooth muscle, inflammation, pain, edema, as well as alteration in the respiratory, cardiovascular and venous systems.

Therefore, PAF-antagonistic activity-possessing compounds are considered to be very useful for various PAF-induced diseases such as inflammatory diseases, allergic diseases, anaphylactic shocks, septic shocks, vascular diseases as DIC, myocardial diseases, asthma, pulmonary edema or adult respiratory diseases.

Japanese Journal of Pharmacology, vol. 44, pp. 381–391 (1987) discloses that antianxietic or anticonvulsant Etizolam (Recommended INN of 6-(o-chlorophenyl)-8-ethyl-1-methyl-4H-s-triazolo[3,4-c]thieno[2,3-e][1,4]diazepine) exhibits antagonistic activity on PAF. EP-A 194416 discloses that thienotriazolo-1,4-diazepine-2-carboxylic acid amide compounds represented by 4-(2-chlorophenyl)-9-methyl-6H-thieno[3,2-f][1,2,4]triazolo[4,3-a][1,4]diazepine-2-propionic acid morpholide exhibit antagonistic activity on PAF, and also EP-A 230942, EP-A 240899 and EP-A 254245 disclose 1,4-diazepine derivatives with PAF antagonistic activity, respectively.

Recently, 3-[4-(2-chlorophenyl)-9-methyl-6H-thieno[3,2-f][1,2,4]triazolo[4,3-a][1,4]diazepin-2-yl]propionic acid morpholide (WEB 2086) or 5-(2-chlorophenyl)-3,4-dihydro-10-methyl-3-morpholinomethyl-2H,7H-cyclopenta[4,5]thieno[3,2-f][1,2,4]triazolo[4,3-a][1,4]diazepine (STY 2108) are known to exhibit more potent PAF-antagonistic activity However, such compounds are not yet sufficient in view of the separation from the effect on the central nervous system, the potency, the effectiveness by the oral administration or the duration of activity Therefore, it is desirable to provide potent PAF-antagonistic compounds which possess not only effectiveness by oral administration and long-lasting effect, but also less inhibitory effect on the central nervous system.

The present inventors have made intensive investigations in view of the above respects and found in a series of the investigations that an introduction of substituent such as alkyl into the diazepine core of the thienotriazolodiazepine compounds has made the PAF-antagonistic activity more potent, effective by oral administration and long-lasting, and furthermore it has made easier to separate the activity from the effect on the central nervous system such as sedative activity or muscle relaxation activity because such activities remarkably decreased, and finally completed the present invention.

SUMMARY OF THE INVENTION

The present invention provides novel and pharmaceutically useful thienotriazolodiazepine compounds which are substituted by an alkyl group on diazepine core thereof or pharmaceutically acceptable acid addition salts thereof, and pharmaceutical uses thereof as PAF antagonists.

DETAILED DESCRIPTION

The present invention relates to a thienotriazolodiazepine compound of the formula:

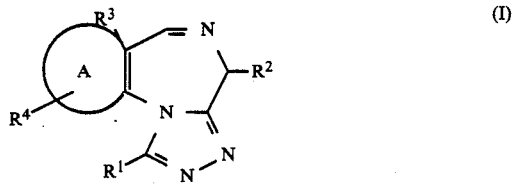

(I)

or a pharmaceutically acceptable salt thereof, wherein $R^1$ is hydrogen, alkyl, substituted alkyl, cycloalkyl, substituted cycloalkyl, alkoxy, substituted alkoxy, halogen, aryl, substituted aryl, aralkyl, substituted aralkyl, cycloalkylalkyl or substituted cycloalkylalkyl;

$R^2$ is alkyl having 1 to 6 carbon atoms or trifluoromethyl;

$R^3$ is phenyl, substituted phenyl, pyridyl or substituted pyridyl;

$R^4$ is a group represented by the formula: $-B_lR^5$, $-D_m-CO->AS\leq_n-R^6$ or

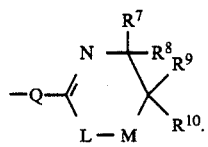

In the formula of $-B_lR^5$, when $l>0$, $R^5$ is hydroxy; halogen; a group represented by $-N(R^{11})(R^{12})$ [wherein $R^{11}$ and $R^{12}$ are the same or different and each is hydrogen; straight or branched chain alkyl, alkenyl or alkynyl having 1 to 10 carbon atoms, which may be optionally substituted by halogen, hydroxy, amino, alkylamino, dialkylamino, cyclic amino or C-binding heterocycle (carbon chain may be optionally interrupted by nitrogen, oxygen or sulfur atom); straight or branched chain alkylcarbonyl having 2 to 6 carbon atoms, which may be optionally substituted by hydroxy, halogen, amino, alkylamino, dialkylamino, cyclic amino or 1 or 2 straight or branched chain alkyl (said alkyl may be optionally substituted by halogen or hydroxy) having 1 to 6 carbon atoms; arylcarbonyl substituted by optional substituent(s); alkylsulfonyl having 1 to 4 carbon atoms; or $R^{11}$ and $R^{12}$ together with the adjacent nitrogen atom form saturated or unsaturated 3- to 7-membered heterocycle optionally having nitrogen, oxygen or sulfur atom as hetero atom in the cycle (each additional nitrogen atom may be optionally substituted by straight or branched chain alkyl having 1 to 4 carbon atoms), which may be optionally mono- or poly-substituted by straight or branched chain alkyl having 1 to 4 carbon atoms.]; arylsulfonyloxy which may be optionally mono- or poly-substituted by straight or branched chain alkyl and/or alkoxy having 1 to 4 carbon atoms;

straight or branched chain alkylsulfonyloxy having 1 to 4 carbon atoms; arylcarbonyloxy which may be optionally mono- or poly-substituted by straight or branched chain alkyl and/or alkoxy having 1 to 4 carbon atoms; straight or branched chain alkylcarbonyloxy (said alkyl may be optionally interrupted by nitrogen, oxygen or sulfur atoms) having 2 to 12 carbon atoms; groups represented by $R^{13}NHCOO-$, $R^{13}NHCON(R^{14})-$ (wherein $R^{13}$ is straight or branched chain alkyl, alkenyl or alkynyl having 1 to 4 carbon atoms, which may be optionally substituted by halogen, or aryl which may be optionally mono- or poly-substituted by straight or branched chain alkyl and/or alkoxy having 1 to 4 carbon atoms, and $R^{14}$ is hydrogen, or straight or branched chain alkyl having 1 to 4 carbon atoms); a group represented by $(R^{15})(R^{16})NSO_2-$ [wherein $R^{15}$ and $R^{16}$ are the same or different and each is straight or branched chain alkyl having 1 to 4 carbon atoms, or $R^{15}$ and $R^{16}$ together with the adjacent nitrogen atom form 3- to 7-membered heterocycle optionally having nitrogen, oxygen or sulfur atom as hetero atom in the cycle (each additional nitrogen atom may be optionally substituted by straight or branched chain alkyl having 1 to 4 carbon atoms), which may be optionally mono- or poly-substituted by straight or branched chain alkyl having 1 to 4 carbon atoms.]; straight or branched alkoxy having 1 to 4 carbon atoms; aryloxy; substituted phenoxy; imino; dioxolan; or substituted dioxolan, and when $l \geq 0$, $R^5$ is $-CHO$; $-COOH$; cyano; straight or branched chain alkoxycarbonyl having 1 to 4 carbon atoms; aryloxycarbonyl; or a group represented by $(R^{17})(R^{18})NCO-$[-wherein $R^{17}$ and $R^{18}$ are the same or different and each is hydrogen phenyl, substituted phenyl, aralkyl or straight or branched chain alkyl, alkenyl or alkynyl having 1 to 10 carbon atoms, which may be optionally substituted by halogen, hydroxy, nitro, amino or substituted amino, or $R^{17}$ and $R^{18}$ together with the adjacent nitrogen atom form 3- to 7-membered heterocycle optionally having nitrogen, oxygen or sulfur atom as hetero atom in the cycle (each additional nitrogen atom may be optionally substituted by straight or branched chain alkyl having 1 to 4 carbon atoms or aralkyl), which may be optionally mono- or poly-substituted by straight or branched chain alkyl having 1 to 4 carbon atoms.], B is straight or branched chain alkylene having l carbon atoms and optionally having at least one double bond in the chain, or which may be optionally substituted by aryl or substituted phenyl, or optionally di-substituted by $R^5$, wherein $R^5$ is optionally the same or different, l is 0, 1, 2, 3, 4, 5, 6, 7, 8, 9 or 10.

In the formula of $-D_m-CO-<AS>_n-R^6$, D is straight or branched chain alkylene having m carbon atoms, $<AS>$ is amino acid or peptide residue which is linked by N-terminal, or amino acid residue represented by the formula:

$$-N(R^{19})-[C(R^{20})(R^{21})]_p-CO-$$
8 wherein $R^{19}$ is hydrogen or straight or branched chain alkyl having 1 to 5 carbon atoms, $R^{20}$ and $R^{21}$ are the same or different and each is hydrogen, straight or branched chain alkyl, alkenyl or alkynyl having 1 to 10 carbon atoms, cycloalkyl having 3 to 7 carbon atoms, aryl or aralkyl, and when $R^{20}$ and/or $R^{21}$ are alkyl, the $R^{20}$ and/or $R^{21}$ may be optionally substituted by one or not less than two hydroxy, alkoxy, cycloalkyl having 3 to 7 carbon atoms, halogen, 1 or 2 straight or branched chain alkyl having 1 to 4 carbon atoms, amino which may be optionally substituted by alkyloxycarbonyl or aralkoxycarbonyl, guanidino, ureido, acyloxy, carboxy, alkoxycarbonyl, cyano, carboxyamido, alkylcarbonyl, mercapto, alkylthio, benzylthio, alkylsulfoxyl, alkylsulfonyl, 3-indolyl, imidazolyl, pyrazolyl and/or amido represented by the formula;

$$-CON(R^{22})(R^{23})$$

(wherein $R^{22}$ and $R^{23}$ are the same or different and each is hydrogen or straight or branched chain alkyl, alkenyl or alkynyl having 1 to 4 carbon atoms, and said alkyl may be optionally substituted by amino or hydroxy, and said amino may be optionally substituted by 1 or 2 straight or branched chain alkyls having 1 to 4 carbon atoms, or $R^{22}$ and $R^{23}$ together form 3- to 7-membered heterocycle optionally having nitrogen, oxygen or sulfur atom as hetero atom in the cycle, which may be optionally substituted by at least one straight or branched chain alkyl having 1 to 4 carbon atoms.) and when $R^{20}$ and/or $R^{21}$ are aryl or aralkyl, the aromatic ring of $R^{20}$ and/or $R^{21}$ may be optionally substituted by at least one hydroxy, halogen, amino or straight or branched chain alkylamino, dialkylamino or alkoxy having 1 to 4 carbon atoms.]$R^6$ is straight or branched chain alkoxy or alkylthio having 1 to 4 carbon atoms, which may be optionally substituted by amino represented by $-N(R^{22})(R^{23})$ (wherein $R^{22}$ and $R^{23}$ are as defined above) or $R^6$ is amino represented by $-N(R^{22})(R^{23})$ (wherein $R^{22}$ and $R^{23}$ are as defined above), $R^{20}$ and $R^{21}$ together form 5- to 7-membered cycle optionally having nitrogen, oxygen or sulfur atom as hetero atom, which may be optionally substituted by at least one straight or branched chain alkyl having 1 to 4 carbon atoms, $R^{19}$ and $R^{20}$ or $R^{21}$ together form 4- to 7-membered cycle optionally having nitrogen, oxygen or sulfur atom as hetero atom, which may be optionally substituted by at least one straight or branched chain alkyl having 1 to 4 carbon atoms, and $R^{20}$ or $R^{21}$ and $R^6$ may optionally form 5- to 7-membered cycle represented by

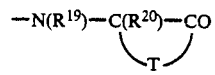

(wherein T is nitrogen, oxygen or sulfur atom, and the cycle may be optionally substituted by straight or branched chain alkyl having 1 to 4 carbon atoms), m is 0, 1, 2, 3, 4, 5, 6, 7 or 8, p is 1, 2, 3, 4, 5, 6, 7 or 8 and n is 1, 2 or 3.

In the formula of

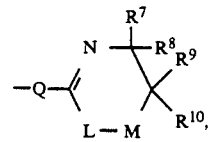

each of L and M is oxygen, sulfur, $-NR^{24}-$ (wherein $R^{24}$ is hydrogen or straight or branched chain alkyl having 1 to 6 carbon atoms) or $(CR^{25}R^{26})_q$ (wherein each of $R^{25}$ and $R^{26}$ is hydrogen, straight or branched chain alkyl having 1 to 6 carbon atoms, which may be optionally substituted by hydroxy or amino, or phenyl, and q is 0, 1, 2 or 3) independently, $R^7$ is hydrogen, straight or branched chain alkyl having 1 to 6 carbon atoms, which may be optionally substituted by hydroxy or amino, or straight or branched chain alkoxycarbonyl having 1 to 4 carbon atoms or dialkylaminocarbonyl of which each alkyl is independently straight or branched chain alkyl having 1 to 4 carbon atoms, $R^8$, $R^9$ and $R^{10}$ are hydrogen, straight or branched chain alkyl having 1 to 6 carbon atoms, which may be optionally substituted by hydroxy or amino, or phenyl, and Q is single bond or straight or branched chain alkylene having 1 to 6 carbon atoms.

Ring A is thiophene ring, tetrahydrobenzothiophene ring or 4,5-dihydro-6H-cyclopenta[b]thiophene ring.

The present invention also provides a pharmaceutical composition comprising the thienotriazolodiazepine compound of formula (I).

The above-mentioned symbols are defined in detail below.

Alkyl means straight or branched chain alkyl having 1 to 6 carbon atoms such as methyl, ethyl, propyl, isopropyl, butyl, isobutyl, tert-butyl, pentyl, isopentyl, neopentyl or hexyl;

Substituted alkyl means alkyl substituted by at least one hydroxy, halogen (e.g. chlorine, bromine or fluorine), amino, nitro, cyano such as hydroxymethyl, 2-hydroxyethyl, chloromethyl, trifluoromethyl, trichloroethyl, aminomethyl, nitromethyl or cyanomethyl;

Cycloalkyl means cycloalkyl having 3 to 7 carbon atoms such as cyclopropyl, cyclopentyl or cyclohexyl;

Substituted cycloalkyl means cycloalkyl substituted by alkyl (e.g. methyl or ethyl) such as 1-methylcyclohexyl;

Alkoxy means straight or branched alkoxy having 1 to 6 carbon atoms such as methoxy, ethoxy, propoxy, isopropoxy, butoxy, isobutoxy, tert-butoxy, pentyloxy, isopentyloxy, neopentyloxy or hexyloxy;

Substituted alkoxy means alkoxy substituted by at least one hydroxy, halogen, amino, nitro or cyano such as hydromethoxy, 2-hydroxyethoxy, chloromethoxy, aminomethoxy, 2-aminoethoxy, nitromethoxy or cyanomethoxy;

Halogen means chlorine, bromine, fluorine or iodine;

Aryl means phenyl or naphthyl;

Substituted aryl means aryl substituted by at least one above-mentioned alkyl, substituted alkyl, alkoxy substituted alkoxy, hydroxy, halogen, amino, nitro or cyano such as 4-methylphenyl, 2-ethylphenyl, 2-chloromethylphenyl, 4-methoxyphenyl, 3,4,5-trimethoxyphenyl, 4-(2-aminoethoxy) phenyl, 2-chlorophenyl, 4-aminophenyl, 4-nitrophenyl or 4-cyanophenyl;

Aralkyl means, for example, benzyl, benzhydryl, triphenylmethyl, 2-phenylethyl, 1-phenylethyl, 3-phenylpropyl or 4-phenylbutyl;

Substituted aralkyl means aralkyl substituted by at least one above-mentioned alkyl, substituted alkyl, alkoxy, substituted alkoxy, hydroxy, halogen, amino, nitro or cyano such as 4-methylbenzyl, 2-trifluorobenzyl, 4-methoxybenzyl, 4-(2-aminoethoxy)benzyl, 2-chlorobenzyl, 4-aminobenzyl, 4-nitrobenzyl, 4-cyanobenzyl or 2-(4-chlorophenyl)ethyl;

Cycloalkylalkyl means above-mentioned alkyl substituted by above-mentioned cycloalkyl such as cyclopropylmethyl, cyclopentylmethyl, cyclohexylmethyl or 2-(cyclohexyl)ethyl;

Substituted cycloalkylalkyl means above-mentioned alkyl substituted by above-mentioned substituted cycloalkyl such as 1-methylcyclohexylmethyl or 2-(1-methylcyclohexyl)ethyl;

Substituted phenyl means phenyl substituted by at least one alkyl, substituted alkyl, alkoxy, substituted alkoxy, hydroxy, halogen, amino, nitro or cyano on the phenyl core such as 4-methylphenyl, 2-ethylphenyl, 2-chloromethylphenyl, 4-methoxyphenyl, 3,4,5-trimethoxyphenyl, 4-(2-aminoethoxy)phenyl, 2-chlorophenyl, 4-aminophenyl, 4-nitrophenyl or 4-cyanophenyl;

Pyridyl means 2-pyridyl, 3-pyridyl or 4-pyridyl;

Substituted pyridyl means pyridyl substituted by alkyl (e.g. methyl or ethyl), alkyl substituted by halogen (e.g. trifluoromethyl) or halogen such as 6-methyl-2-pyridyl, 6-trifluoromethyl-2-pyridyl or 6-chloro-2-pyridyl;

Straight or branched chain alkyl, alkenyl or alkynyl having 1 to 10 carbon atoms, which may be optionally substituted by halogen, hydroxy, amino, alkylamino, dialkylamino, cyclic amino or C-binding heterocycle (carbon chain may be optionally interrupted by nitrogen, oxygen or sulfur atom) includes, for example, methyl, ethyl, propyl, isopropyl, butyl, isobutyl, tert-butyl, pentyl, isopentyl, neopentyl, hexyl, octyl, decyl, vinyl, allyl, isopropenyl, 2-butenyl, ethynyl, 2-propynyl, chloromethyl, trifluoromethyl, 2-hydroxyethyl, aminomethyl, methylaminomethyl, dimethylaminomethyl, 2-dimethylaminoethyl, 2-morpholinoethyl, 2-piperidinoethyl, furfuryl, 2-(2-indolyl)ethyl, 2-thenyl, 2-pyridylmethyl, 2quinolylmethyl or 2-pyrimidinylmethyl;

Straight or branched chain alkylcarbonyl having 2 to 6 carbon atoms, which may be optionally substituted by hydroxy, halogen, amino, alkylamino, dialkylamino, cyclic amino or 1 or 2 straight or branched chain alkyl (said alkyl may be optionally substituted by halogen or hydroxy) having 1 to 6 carbon atoms includes, for example, acetyl, propionyl, butyryl, isobutyryl or pivaloyl, or substituted thereof by hydroxy, chloro, amino, methylamino, dimethylamino, morpholino, methyl or ethyl;

Arylcarbonyl substituted by optional substituent(s) includes, for example, benzoyl, 4-hydroxybenzoyl, 2-chlorobenzoyl or 4-methylbenzoyl;

Arylsulfonyl substituted by optional substituent(s) includes, for example, phenylsulfonyl, 4-methylphenylsulfonyl, 4-aminophenylsulfonyl or 4-acetylaminophenylsulfonyl;

Alkylsulfonyl having 1 to 4 carbon atoms includes, for example, methanesulfonyl, ethanesulfonyl, propanesulfonyl or butanesulfonyl;

Saturated or unsaturated 3- to 7-membered heterocycle formed with the adjacent nitrogen atom optionally having nitrogen, oxygen or sulfur atom as hetero atom in the cycle (each additional nitrogen atom may be optionally substituted by straight or branched chain alkyl having 1 to 4 carbon atoms), which may be optionally mono- or poly-substituted by straight or branched chain alkyl having 1 to 4 carbon atoms includes, for example, 1-aziridinyl, 1-azetidinyl, 1-pyrrolidinyl, piperidino, 1-piperazinyl, 1-azepinyl, 1-perhydroazepinyl, morpholino, thiomorpholino, 1-imidazolyl, 4-methyl-1-piperazinyl, 2,6-dimethylmorpholino, 1,2,4-triazol-1-yl, 1-pyrazolyl or 1-pyrrolyl;

Arylsulfonyloxy which may be optionally mono- or polysubstituted by straight or branched chain alkyl and/or alkoxy having 1 to 4 carbon atoms means, preferably, 4-methylphenylsulfonyloxy or phenylsulfonyloxy;

Straight or branched chain alkylsulfonyloxy having 1 to 4 carbon atoms includes, for example, methanesulfonyloxy, ethanesulfonyloxy, isopropylsulfonyloxy or butanesulfonyloxy;

Arylcarbonyloxy which may be optionally mono- or polysubstituted by straight or branched chain alkyl and/or alkoxy having 1 to 4 carbon atoms means, preferably, benzoyloxy or 4-methylbenzoyloxy;

Straight or branched chain alkylcarbonyloxy (said alkyl may be optionally interrupted by nitrogen, oxygen or sulfur atoms) having 2 to 12 carbon atoms includes, for example, acetoxy, propionyloxy, butyryloxy, pivaloyloxy or valeryloxy;

Straight or branched chain alkyl, alkenyl or alkynyl having 1 to 4 carbon atoms, which may be optionally substituted by halogen includes, for example, methyl, ethyl, propyl, isopropyl, butyl, isobutyl, tert-butyl, vinyl, allyl, isopropenyl, 2-butenyl, ethynyl, 2-propynyl, chloromethyl, 2-chloroethyl or trifluoromethyl;

Aryl which may be optionally mono- or poly-substituted by straight or branched chain alkyl and/or alkoxy having 1 to 4 carbon atoms includes, for example, phenyl, 4-methylphenyl, 2-methoxyphenyl or 3,4,5-trimethoxyphenyl;

Straight or branched chain alkyl and/or alkyl having 1 to 4 carbon atoms in $R^{14}$ includes, for example, methyl, ethyl, propyl, isopropyl, butyl, isobutyl or tert-butyl;

Aryloxy means, preferably, phenoxy;

Substituted phenoxy means phenoxy which is substituted by at least one straight or branched chain alkyl and/or alkoxy having 1 to 4 carbon atoms, alkyl substituted by halogen, or hydroxy, halogen, amino, nitro or cyano and includes, for example, 4-methylphenoxy, 4-methoxyphenoxy, 2-trifluoromethylphenoxy, 2-hydroxyphenoxy, 2-chlorophenoxy, 4-aminophenoxy, 4-nitrophenoxy, 4-cyanophenoxy or 3,4,5-trimethoxyphenoxy;

Imino means phthalimido, succinimido or 2,5-dioxoimidazolidin-1-yl;

Straight or branched chain alkoxycarbonyl having 1 to 4 carbon atoms includes, for example, methoxycarbonyl, ethoxycarbonyl, propoxycarbonyl, isopropoxycarbonyl, butoxycarbonyl or tert-butoxycarbonyl;

Aryloxycarbonyl means, preferably, phenoxycarbonyl;

Straight or branched chain alkyl, alkenyl or alkynyl having 1 to 10 carbon atoms, which may be optionally substituted by halogen, nitro, amino or substituted amino means, preferably, chloromethyl or 2-dimethylaminoethyl;

Straight or branched chain alkylene means 1 or m alkylene chains and includes, for example, methylene, ethylene, trimethylene, propylene, tetramethylene, pentamethylene, hexamethylene, octamethylene or decamethylene;

Acyloxy includes, for example, acetoxy, propionyloxy, butyryloxy, pivaloyloxy or benzoyloxy;

Alkylthio includes, for example, methylthio, ethylthio, propylthio, isopropylthio, butylthio, isobutylthio, tertbutylthio, pentylthio or hexylthio;

Alkylsulfoxyl includes, for example, methylsulfoxyl, ethylsulfoxyl or butylsulfoxyl;

Alkylsulfonyl includes, for example, methylsulfonyl, ethylsulfonyl or butylsulfonyl;

Straight or branched chain alkyl, alkenyl or alkynyl having 1 to 4 carbon atoms includes, for example, methyl, ethyl, propyl, isopropyl, butyl, isobutyl, tertbutyl, vinyl, allyl, isopropenyl, 2-butenyl, ethynyl or 2-propynyl;

Straight or branched chain alkyl having 1 to 6 carbon atoms, which may be optionally substituted by hydroxy or amino includes, for example, methyl, ethyl, propyl, isopropyl, butyl, isobutyl, tert-butyl, pentyl, isopentyl, neopentyl, hexyl, hydroxymethyl, 2-hydroxyethyl, aminomethyl or 2-aminoethyl;

Dialkylaminocarbonyl of which each alkyl is independently straight or branched chain alkyl having 1 to 4 carbon atoms includes, for example, dimethylaminocarbonyl, diethylaminocarbonyl, dipropylaminocarbonyl, diisopropylaminocarbonyl, dibutylaminocarbonyl, diisobutylaminocarbonyl or ditertbutylaminocarbonyl;

Ring A means as follows:

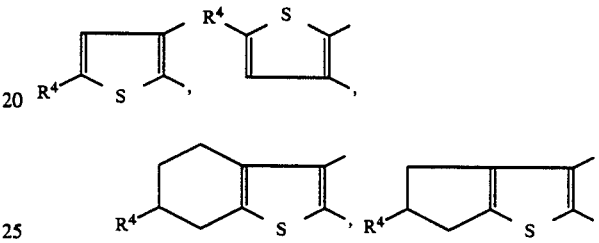

Preferable compounds of the present invention are the compound of formula (I) or a pharmaceutically acceptable salt thereof wherein $R^4$ is-$B_1R^5$, wherein $R^5$ B and l are as defined above.

More preferable compounds of the present invention are the compound of formula (I) or a pharmaceutically acceptable acid addition salt thereof wherein $R^4$ is-$B_1R^5$, wherein when l>0, $R^5$ is hydroxy; halogen; a group represented by

—N($R^{11}$)($R^{12}$)

[wherein $R^{11}$ and $R^{12}$ are the same or different and each is hydrogen; straight or branched chain alkyl, alkenyl or alkynyl having 1 to 10 carbon atoms; straight or branched chain alkylcarbonyl having 2 to 6 carbon atoms; arylcarbonyl; or $R^{11}$ and $R^{12}$ together with the adjacent nitrogen atom form saturated or unsaturated 3- to 7-membered heterocycle optionally having nitrogen, oxygen or sulfur atom as hetero atom in the cycle (each additional nitrogen atom may be optionally substituted by straight or branched chain alkyl having 1 to 4 carbon atoms)]; arylsulfonyloxy which may be optionally mono- or poly-substituted by straight or branched chain alkyl and/or alkoxy having 1 to 4 carbon atoms; straight or branched chain alkylsulfonyloxy having 1 to 4 carbon atoms; straight or branched chain alkylcarbonyloxy having 1 to 12 carbon atoms; a group represented by ($R^{15}$)($R^{16}$)NSO$_2$— [wherein $R^{15}$ and $R^{16}$ are the same or different and each is straight or branched chain alkyl having 1 to 4 carbon atoms, or $R^{15}$ and $R^{16}$ together with the adjacent nitrogen atom form 3- to 7-membered heterocycle optionally having nitrogen, oxygen or sulfur atom as hetero atom in the cycle (each additional nitrogen atom may be optionally substituted by straight or branched chain alkyl having 1 to 4 carbon atoms)]; or imino, and when l≧0, $R^5$ is a group represented by ($R^{17}$)($R^{18}$)NCO—[wherein $R^{17}$ and $R^{18}$ are the same or different and each is hydrogen, aralkyl or straight or branched chain alkyl, alkenyl or alkynyl having 1 to 10 carbon atoms, or $R^{17}$ and $R^{18}$ together with the adjacent nitrogen atom form 3- to 7-membered heterocycle optionally having nitrogen, oxygen or sulfur atom as hetero atom in the cycle (each additional nitrogen atom may be optionally substituted by straight or branched chain alkyl having 1 to 4 carbon atoms or aralkyl)], B is straight or branched chain alkylene having 1 carbin atoms and optionally having at least one double bond in the chain, l is 0, 1, 2, 3, 4, 5, 6, 7, 8, 9 or 10.

Specific compounds of the present invention are, for example,

3-[4-(2-chlorophenyl)-6,9-dimethyl-6H-thieno[3,2-f][1,2,4]triazolo[4,3-a][1,4]diazepin-2-yl]propionic acid morpholide, 5-(2-chlorophenyl)-3,4-dihydro-7,10-dimethyl-3-morpholinocarbonyl-2H,7H-cyclopenta[4,5]thieno[3,2-f][1,2,4]triazolo4,3-a][1,4]diazepine, 5-(2-chlorophenyl)-3,4-dihydro-7,10-dimethyl-3-morpholinomethyl-2H,7H-cyclopenta[4,5]thieno[3,2-f][1,2,4]triazolo[4,3-a]-1,4]diazepine, 2-(2-chlorophenyl)-3,4-dihydro-7,10-dimethyl-3-thiomorpholinocarbonyl-2H,7H-cyclopenta[4,5]-thieno[3,2-f][1,2,4]triazolo[4,3-a][1,4]diazepine, 6-(2-chlorophenyl)-2,3,4,5-tetrahydro-8,11-dimethyl-3-morpholinocarbonyl-8-(1)benzothieno[3,2-f][1,2,4]triazolo[4,3-a][1,4]-diazepine, 3-[4-(2-chlorophenyl)-6,9-dimethyl-6H-thieno[3,2-f][1,2,4]-triazolo[4,3-a][1,4]diazepin-2-yl]propionic acid 4-isobutyl-1-piperazide, 3-[4-(2-chlorophenyl)-6,9-dimethyl-6H-thieno[3,2-f][1,2,4]triazolo[4,3-a][1,4]diazepin-2-yl]propionic acid N,N-dipropylamide, 3-[4-(2-chlorophenyl)-6,9-dimethyl-6H-thieno[3,2-f][1,2,4]-triazolo[4,3-a][1,4]diazepin-2-yl]propionic acid piperidide, 4-(2-chlorophenyl)-6,9-dimethyl-2-(6-morpholinohexyl)-6H-thieno[3,2-f][1,2,4]triazolo[4,3-a][1,4]diazepine and 4-(2-chlorophenyl)-6,9-dimethyl-2-(3-morpholinopropyl)-6H-thieno[3,2-f][1,2,4]triazolo[4,3-a][1,4]diazepine, or a pharmaceutically acceptable acid addition salt thereof.

Generally, the compound of formula (I) of the present invention can be prepared from the corresponding thienodiazepinethione compound by using known methods, and also can be prepared by converting the functional groups of the side chains in the thus obtained thienotriazolodiazepine compound in a usual manner. For example, the compound of formula (I) can be prepared by reacting a thienodiazepinethione compound of the formula:

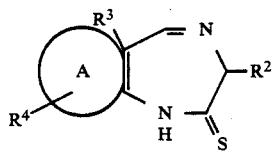 (II)

wherein each symbol is as defined above,
(a) with a compound of the formula:

R$^1$—CONHNH$_2$ (III)

wherein R$^1$ is as defined above, or (b) by reacting a hydrazide compound obtained by a reaction of the compound (II) with hydrazine, with a compound of the formula:

R$^1$—CO—Hal (IV)

wherein R$^1$ is as defined above and Hal is halogen such as chlorine, or with a compound of the formula:

R$^1$—C(OR′)$_3$ (V)

wherein R$^1$ is as defined above and R′ is alkyl such as methyl or ethyl.

The reaction of the process (a) is usually carried out at a temperature of from room temperature to the refluxing temperature of the solvent employed in an inert solvent such as benzene, toluene, tetrahydrofuran, dioxane or dimethylformamide. The reaction of the compound (II) with hydrazine in the process (b) is usually carried out at a temeperature of room temperature to the refluxing temperature of the solvent employed in an inert solvent such as benzene, toluene, methylene chloride, tetrahydrofuran or dioxane. The subsequent reaction with the compound (IV) or (V) is usually carried out either in an inert solvent such as methylene chloride, diethyl ether, tetrahydrofuran or dioxane or without any solvent.

A carboxamide compound of the compound (I) can be prepared by reacting the corresponding carboxylic acid compound or reactive derivative thereof (e.g. carboxylic acid halide or carboxylic anhydride) with a compound of the formula:

HN(R$^{17}$)(R$^{18}$) (VI)

wherein each symbol is as defined above.

A compound of the formula (I) wherein R$^5$ is R$^{13}$NHCOO— or R$^{13}$NHCON(R$^{14}$)— can be prepared by reacting the corresponding alcohol or amine compound with a desired isocyanate compound in an inert solvent such as methylene chloride or tetrahydrofuran, preferably, under heating in the presence of a base (e.g. 1,4-diazabicyclo[2,2,2]octane).

A compound of the formula (I) wherein R$^5$ is alkylcarbonyloxy or arylcarbonyloxy can be prepared by reacting the corresponding alcohol compound of compound (I) with a carboxylic acid compound or reactive derivative thereof (e.g. carboxylic acid halide or carboxylic anhydride).

A compound of the formula (I) wherein R$^5$ is alkylsulfonyloxy or arylsulfonyloxy can be prepared by reacting, preferably, the corresponding alcohol compound of compound (I) with a sulfonic acid halide compound in an inert solvent such as methylene chloride in the presence of a base such as triethylamine.

A compound of the formula (I) wherein R$^5$ is —N(R$^{11}$)(R$^{12}$) or imino can be prepared by reacting the thus obtained sulfonate compound, preferably mesylate compound, with an amine or imino-forming compound such as phthalimido, and the compound (I) wherein R$^5$ is aryloxy or alkoxy can be prepared by reacting the sulfonate compound with the corresponding alkoxide compound.

A compound of the formula (I) wherein R$^5$ is amino can be prepared by subjecting the corresponding phthalimido compound to the well known elimination reaction.

A compound of the forumula (I) wherein R$^{11}$ or R$^{12}$ is alkylcarbonyl or arylcarbonyl can be prepared by reacting the thus obtained amine compound with a reactive derivative of carboxylic acid compound.

A compound of the formula (I) wherein R$^5$ is cyano can be prepared by reacting the corresponding primary carboxamide compound with phosphorus oxychloride under refluxing in an inert solvent such as dichloroethane.

A compound of the formula (I) wherein $R^5$ is halogen atom can be prepared by reacting a compound (I) wherein $R^5$ is tosylate with a corresponding halogenating agent in, for example, acetone.

A compound of the formula (I) wherein $R^4$ is a group represented by —Dm—CO—<AS>n—$R^6$ can be prepared by reacting the corresponding thieno-triazolodiazepine compound wherein $R^4$ is —D$_m$—COOH with a compound represented by the formula:

  (VII)

wherein each symbol is as defined above, in the presence of carbodiimide, or by reacting a reactive derivative of the above carboxylic acid compound (e.g. carboxylic acid halide, mixed acid anhydride or carboxylic acid imidazolidide) with a compound (VII).

The reaction of the carboxylic acid compound with the compound (VII) is carried out, preferably, at 0° C. to room temperature in an inert solvent such as dimethylformamide, tetrahydrofuran or dioxane in the presence of carbodiimide such as cyclohexylcarbodiimide, and the reaction of the reactive derivative of the carboxylic acid compound with the compound (VII) is carried out in a similar manner, preferably, in the presence of a base such as sodium carbonate, sodium hydrogencarbonate, triethylamine or pyridine.

A compound of the formula (I) wherein $R^6$ is amino or N($R^{22}$)($R^{23}$) can be prepared by reacting a compound wherein $R^4$ is —Dm—CO—<AS>$_n$—OH with the corresponding amine compound using a known method.

A compound of the formula (I) wherein $R^4$ is a group represented by

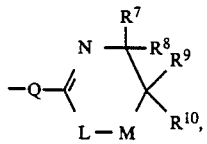

especially said heterocycle is oxazoline, thiazoline or imidazoline nucleus, can be prepared by reacting the corresponding carboxylic acid compound with an amino-alcohol, amino-mercaptan or diamine in acetonitrile in the presence of triphenylphosphine, carbon tetrachloride and tertiary organic base, preferably at 0° C. to room temperature. The corresponding 6- and 7-membered heterocycle compound can be prepared in a similar manner. The compound (I) wherein said heterocycle is oxazoline can be prepared by cyclization of the corresponding hydroxylated carboxyamide with thionyl chloride in an inert organic solvent, and, if desired, the corresponding thiazoline compound can be prepared by thionating the compound with phosphorus pentasulfide or Lawesson agent.

Furthermore, the imidazoline compound substituted by alkyl on the heterocycle can be prepared by treating the corresponding cyano compound with excess ethanolic hydrochloric acid, reacting the obtained imidoethyl ester hydrochloride with a diamine such as ethylenediamine in ethanol, and then by N-alkylating the thus obtained 2-imidazoline compound.

The starting compounds of formula (II) are also novel and can be prepared, for example, as follows:
A compound of the formula:

  (VIII)

the formula:

  (IX)

wherein $R^4$ is as defined above, in the presence of sulfur in a solvent such as an alcohol (e.g. methanol or ethanol), dimethylformamide or dimethylacetamide with a base catalyst such as triethylamine, pyrrolidine, piperidine or morpholine at room temperature to 100° C., to give a compound of the formula:

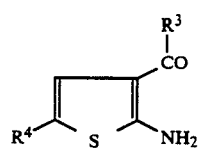  (X)

wherein each symbol is as defined above.

(a) The compound of the formula (X) is reacted with a compound of the formula:

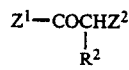  (XI)

wherein $Z^1$ and $Z^2$ are the same or different and each is halogen such as chlorine or bromine, and $R^2$ is as defined above, and, if necessary, a N-haloacetyl compound thus obtained is reacted with potassium iodide or sodium iodide to convert to N-iodoacetyl compoumd, and then reacted with ammonia to give N-glycyl compound.

The reaction is carried out under cooling, at a room temperature or under heating in a solvent such as acetone, tetrahydrofuran or dioxane.

(b) The compound of formula (X) as mentioned above is reacted with a compound of the formula:

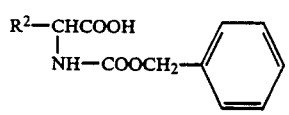  (XII)

wherein $R^2$ is as defined above, in a solvent such as methylene chloride, chloroform or dichloroethane at low temperature and react with thionyl chloride to convert into carboxylic acid halide and then into acetyl compound. The protecting group of said compound is eliminated with hydrobromic acid or hydrochloric acid to give N-glycyl compound.

(c) The compound of formula (X) is reacted with a compound of the formula:

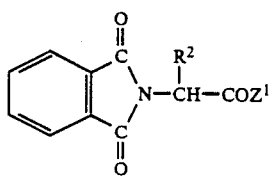  (XIII)

wherein $R^2$ and $Z^1$ are as defined above, to give acetyl compound and then the protecting group of said compound is eliminated according to a conventional manner to give N-glycyl compound.

The thus obtained N-glycyl compound is subjected to ring closure reaction with dehydration at room temperature or under heating in an inert solvent (e.g. ethanol, propanol, isopropyl alcohol, butanol, benzene, toluene, dimethylformamide or dimethylaetamide), preferably in the presence of a weak acid catalyst such as acetic acid, propionic acid or silica gel to give a compound of the formula:

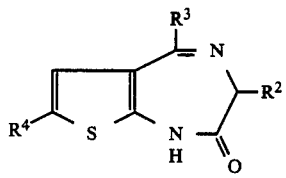

(XIV)

wherein each symbol is as defined above.

Furthermore, the compound of the formula (XIV) is reacted with a thionating agent to give the compound of formula (II).

In the above reaction, thionating agent includes, for example, phosphorus pentasulfide and Lawesson reagent, i.e. 2,4-bis(4-methoxyphenyl)-1,2,3,4-dithiadiphosphetan-2,4,-disulfide.

The reaction of the compound (XIV) with the thionating agent is usually carried out at 30°–100° C. in an inert solvent (e.g. pyridine, dimethylaniline, benzene, toluene, xylene, tetrahydrofuran, chloroform, dioxane or a mixed solvent thereof).

The thus obtained compound of formula (I) can be isolated and purified from the resulting mixture by means of a known and conventional manner such as recrystallization or chromatography.

The compound of formula (I) can be converted into a pharmaceutically acceptable acid addition salt thereof by treating the compound with an inorganic acid (e.g. hydrochloric acid, hydrobromic acid, sulfuric acid, nitric acid or phosphoric acid) or an organic acid (e.g. fumaric acid, maleic acid, succinic acid, citric acid, tartaric acid, methanesulfonic acid, toluenesulfonic acid or pamoic acid).

The compound having carboxyl group can be converted into the corresponding metallic salt thereof (e.g. sodium salt, potassium salt, magnesium salt, calcium salt or aluminium salt) by treating the compound with alkali hydroxide and so on, and also converted into the salt with amine or amino acid (e.g. lysine). The solvate of the compound (I) like hydrate (e.g. ½ hydrate, monohydrate or 3/2 hydrate) can also be encompassed in the scope of the invention.

The compound of the present invention having chiral carbon atom or atoms can be usually prepared as racemate. The racemate can be divided into optical isomers by a conventional method. Such optical isomers can also be prepared by using optically active starting compounds. The individual diastereoisomer can be purified by means of fractional recrystallization or chromatography.

The compounds in the scope of the present invention are exemplified in the following tables, but these compounds are not to be construed as limiting the present invention.

| No. | $R^1$ | $R^2$ | $R^3$ | $R^4$ |
|---|---|---|---|---|
| 1 | CH$_3$ | CH$_3$ | o-chlorophenyl | —(CH$_2$)$_3$OCOCH$_3$ |
| 2 | CH$_3$ | CH$_3$ | o-chlorophenyl | —(CH$_2$)$_3$OH |
| 3 | CH$_3$ | CH$_3$ | o-chlorophenyl | —(CH$_2$)$_2$SO$_2$N(CH$_2$CH$_2$)$_2$NCH$_3$ |
| 4 | CH$_3$ | CH$_3$ | o-chlorophenyl | —(CH$_2$)$_7$OCOCH$_3$ |

-continued

| No. | R¹ | R² | R³ | R⁴ |
|---|---|---|---|---|
| 5 | CH₃ | CH₃ | 2-chlorophenyl | $-(CH_2)_3OCOCH(CH_3)_2$ |
| 6 | CH₃ | CH₃ | 2-chlorophenyl | $-(CH_2)_3OSO_2CH_3$ |
| 7 | CH₃ | CH₃ | 2-chlorophenyl | $-(CH_3)_3I$ |
| 8 | CH₃ | CH₃ | 2-chlorophenyl | $-(CH_2)_7$-phthalimido |
| 9 | CH₃ | CH₃ | 2-chlorophenyl | $-(CH_2)_7NH_2$ |
| 10 | CH₃ | CH₃ | 2-chlorophenyl | $-(CH_2)_7NHCOCH_3$ |
| 11 | CH₃ | CH₃ | 2-chlorophenyl | $-(CH_2)_3N$-morpholino |
| 12 | CH₃ | CH₃ | 2-chlorophenyl | $-(CH_2)_6CHO$ |
| 13 | Br | CH₃ | 2-chlorophenyl | $-(CH_2)_3OCOCH_3$ |
| 14 | CH₃ | CH₃ | 2-chlorophenyl | $-(CH_2)_2CON(C_2H_5)_2$ |
| 15 | CH₃ | CH₃ | 2-chlorophenyl | $-\underset{\underset{CH_3}{\mid}}{C}=CHCON\text{-morpholino}$ |

-continued

| No. | R¹ | R² | R³ | R⁴ |
|---|---|---|---|---|
| 16 | CH₃ | CH₃ | 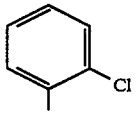 2-Cl-C₆H₄ | —CH₂CH(CH₂CH=CH₂)CON(morpholino) |
| 17 | CH₃ | CH₃ | 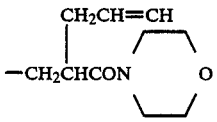 2-Cl-C₆H₄ | —CH₂CH(CH₂C₆H₅)CON(morpholino) |
| 18 | CH₃ | CH₃ | 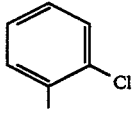 2-Cl-C₆H₄ | —CH₂CH(CH₃)CON(C₂H₅)₂ |
| 19 | CH₃ | CH₃ | 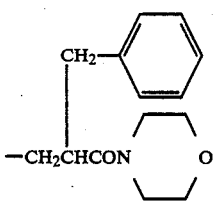 2-Cl-C₆H₄ | —(CH₂)₂-C(=N-C(CH₃)₂CH₂O)— (4,4-dimethyl-2-oxazoline) |
| 20 | CH₃ | CH₃ | 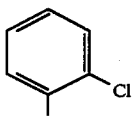 2-Cl-C₆H₄ | —CH₂-(2-phenyl-1,3-dioxol-4-yl) |
| 21 | CH₃ | CH₃ | 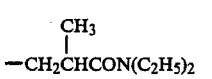 2-Cl-C₆H₄ | —CH₂CH(COOC₂H₅)CON(morpholino) |
| 22 | CH₃ | CH₃ | 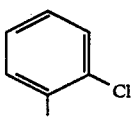 2-Cl-C₆H₄ | —(CH₂)₇OH |
| 23 | CH₃ | CH₃ | 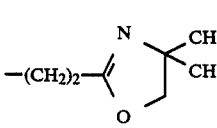 2-Cl-C₆H₄ | —(CH₂)₃Cl |
| 24 | CH₃ | CH₃ | 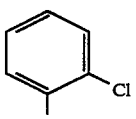 2-Cl-C₆H₄ | —(CH₂)₇Cl |
| 25 | CH₃ | CH₃ | 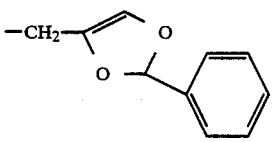 2-Cl-C₆H₄ | —(CH₂)₇I |
| 26 | CH₃ | CH₃ | 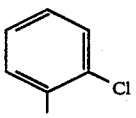 2-Cl-C₆H₄ | —(CH₂)₃NH₂ |

-continued

| No. | R¹ | R² | R³ | R⁴ |
|---|---|---|---|---|
| 27 | CH₃ | CH₃ | 2-chlorophenyl | —(CH₂)₂SO₂N(morpholino) |
| 28 | CH₃ | CH₃ | 2-chlorophenyl | —(CH₂)₃OSO₂CH(CH₃)₂ |
| 29 | CH₃ | CH₃ | 2-chlorophenyl | —(CH₂)₃OSO₂—C₆H₄—CH₃ |
| 30 | CH₃ | CH₃ | 2-chlorophenyl | —(CH₂)₇OSO₂CH₃ |
| 31 | CH₃ | CH₃ | 2-chlorophenyl | —(CH₂)₇OSO₂—C₆H₄—CH₃ |
| 32 | CH₃ | CH₃ | 2-chlorophenyl | —(CH₂)₃OCOC(CH₃)₃ |
| 33 | CH₃ | CH₃ | 2-chlorophenyl | —(CH₂)₇OCOCH(CH₃)₂ |
| 34 | CH₃ | CH₃ | 2-chlorophenyl | —(CH₂)₇OCOC(CH₃)₃ |
| 35 | CH₃ | CH₃ | 2-chlorophenyl | —(CH₂)₇OCONHCH₃ |
| 36 | CH₃ | CH₃ | 2-chlorophenyl | —CH₂N(phthalimido) |
| 37 | CH₃ | CH₃ | 2-chlorophenyl | —(CH₂)₃N(succinimido) |

-continued

| No. | R¹ | R² | R³ | R⁴ |
|---|---|---|---|---|
| 38 | CH₃ | CH₃ | 2-chlorophenyl | —(CH₂)₃N(phthalimido) |
| 39 | CH₃ | CH₃ | 2-chlorophenyl | —(CH₂)₇N(hydantoin-1-yl) |
| 40 | CH₃ | CH₃ | 2-chlorophenyl | —(CH₂)₇N(succinimido) |
| 41 | CH₃ | CH₃ | 2-chlorophenyl | —CH₂NHCOCH₃ |
| 42 | CH₃ | CH₃ | 2-chlorophenyl | —(CH₂)₃NHCOCH₃ |
| 43 | CH₃ | CH₃ | 2-chlorophenyl | —(CH₂)₃NHCOCH(CH₃)₂ |
| 44 | CH₃ | CH₃ | 2-chlorophenyl | —(CH₂)₃NHCO-phenyl |
| 45 | CH₃ | CH₃ | 2-chlorophenyl | —(CH₂)₃NHCH₂N(CH₃)₂ |
| 46 | CH₃ | CH₃ | 2-chlorophenyl | —(CH₂)₃NHSO₂-C₆H₄-NHCOCH₃ |
| 47 | CH₃ | CH₃ | 2-chlorophenyl | —(CH₂)₇NHCOCH(CH₃)₂ |
| 48 | CH₃ | CH₃ | 2-chlorophenyl | —(CH₂)₇NHCO-phenyl |

| No. | R¹ | R² | R³ | R⁴ |
|---|---|---|---|---|
| 49 | $CH_3$ | $CH_3$ | 2-Cl-phenyl | $-(CH_2)_7NHCOCH_2N(CH_3)_2$ |
| 50 | $CH_3$ | $CH_3$ | 2-Cl-phenyl | $-(CH_2)_7NHSO_2$-C$_6$H$_4$-NHCOCH$_3$ |
| 51 | $CH_3$ | $CH_3$ | 2-Cl-phenyl | $-(CH_2)_7N$(morpholino) |
| 52 | $CH_3$ | $CH_3$ | 2-Cl-phenyl | $-(CH_2)_3N$(piperidino) |
| 53 | $CH_3$ | $CH_3$ | 2-Cl-phenyl | $-(CH_2)_3N$(2,6-dimethylmorpholino) |
| 54 | $CH_3$ | $CH_3$ | 2-Cl-phenyl | $-(CH_2)_3N$(2,6-dimethylmorpholino) |
| 55 | $CH_3$ | $CH_3$ | 2-Cl-phenyl | $-(CH_2)_3N$(4-methylpiperazino) |
| 56 | $CH_3$ | $CH_3$ | 2-Cl-phenyl | $-(CH_2)_7N$(4-methylpiperazino) |
| 57 | H | $CH_3$ | 2-Cl-phenyl | $-(CH_2)_3OCOCH_3$ |
| 58 | $CH_3$ | $CH_3$ | phenyl | $-(CH_2)_3OCOCH_3$ |
| 59 | $CH_3$ | $CH_3$ | phenyl | $-(CH_2)_3OH$ |

-continued
| No. | R¹ | R² | R³ | R⁴ |
|---|---|---|---|---|
| 60 | CH₃ | CH₃ | 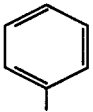 | —(CH₂)₃OSO₃CH₃ |
| 61 | CH₃ | CH₃ | 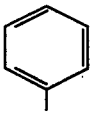 |  |
| 62 | OCH₃ | CH₃ | 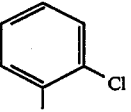 | —(CH₂)₃OCOCH₃ |
| 63 | CH₃ | CH₃ | 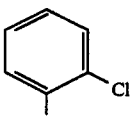 | —(CH₂)₇N(CH₃)₂ |
| 64 | CH₃ | CH₃ | 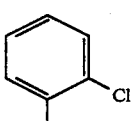 | —(CH₂)₇NH(CH₂)₂N(CH₃)₂ |
| 65 | CH₃ | CH₃ | 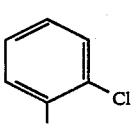 | 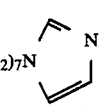 |
| 66 | CH₃ | CH₃ | 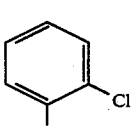 | 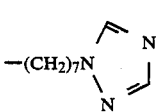 |
| 67 | CH₃ | CH₃ | 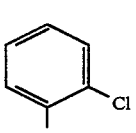 | 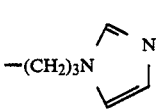 |
| 68 | CH₃ | CH₃ | 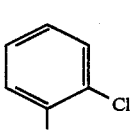 | 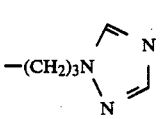 |
| 69 | CH₃ | CH₃ | 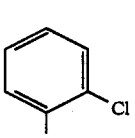 | —(CH₂)₃N(CH₃)₂ |
| 70 | CH₃ | CH₃ | 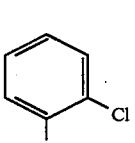 | —(CH₂)₃NH(CH₂)₂N(CH₃)₂ |

-continued

| No. | R¹ | R² | R³ | R⁴ |
|---|---|---|---|---|
| 71 | CH₃ | CH₃ | 2-Cl-C₆H₄ | −(CH₂)₃NHSO₂−C₆H₄−NH₂ |
| 72 | CH₃ | CH₃ | 2-Cl-C₆H₄ | −(CH₂)₇NHSO₂−C₆H₄−NH₂ |
| 73 | CH₃ | CH₃ | 2-Cl-C₆H₄ | −(CH₂)₇N(piperidine) |
| 74 | OCH₃ | CH₃ | 2-Cl-C₆H₄ | −(CH₂)₃OH |
| 75 | CH₃ | CH₃ | 2-Cl-C₆H₄ | −(CH₂)₃N(C₂H₅)₂ |
| 76 | CH₃ | CH₃ | 2-Cl-C₆H₄ | −(CH₂)₃N(pyrazol-1-yl) |
| 77 | CH₃ | CH₃ | 2-Cl-C₆H₄ | −(CH₂)₇N(pyrazol-1-yl) |
| 78 | CH₃ | CH₃ | 2-Cl-C₆H₄ | −(CH₂)₇N(pyrrol-1-yl) |
| 79 | CH₃ | CH₃ | 2-Cl-C₆H₄ | −(CH₂)₃NH(CH₂)₂N(morpholino) |
| 80 | CH₃ | CH₃ | 2-Cl-C₆H₄ | −(CH₂)₇NHCH₂−(2-furyl) |
| 81 | CH₃ | CH₃ | 2-Cl-C₆H₄ | −(CH₂)₇NH(CH₂)₂−(1H-indol-2-yl) |

| No. | R¹ | R² | R³ | R⁴ |
|---|---|---|---|---|
| 82 | CH₃ | CH₃ | 2-chlorophenyl | 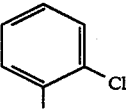 |
| 83 | CH₃ | CH₃ | 2-chlorophenyl | —CH₂CH(COOC₂H₅)₂ |
| 84 | CH₃ | CH₃ | 2-chlorophenyl | 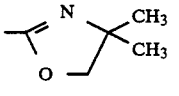 |
| 85 | CH₃ | CH₃ | 2-chlorophenyl | 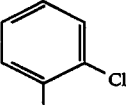 |
| 86 | CH₃ | CH₃ | 2-chlorophenyl | —CH₂CHCH₂OH<br>      OH |
| 87 | CH₃ | CH₃ | 2-chlorophenyl | —CH₂CHCH₂OCOCH₃<br>      OCOCH₃ |
| 88 | CH₃ | CH₃ | 2-chlorophenyl | 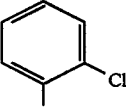 |
| 89 | CH₃ | CH₃ | 2-chlorophenyl | 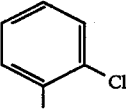 |
| 90 | CH₃ | CH₃ | 2-chlorophenyl | 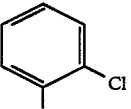 |
| 91 | CH₃ | CH₃ | 2-chlorophenyl | —(CH₂)₃O-phenyl |
| 92 | CH₃ | CH₃ | 2-chlorophenyl | —(CH₂)₃OCH₃ |

-continued

| No. | R¹ | R² | R³ | R⁴ |
|---|---|---|---|---|
| 93 | CH₃ | CH₃ | 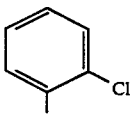 (2-Cl-C₆H₄) | —(CH₂)₃NH(CH₂)₂— 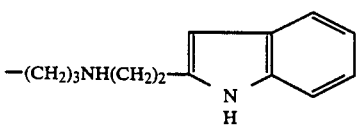 (indol-2-yl) |
| 94 | CH₃ | CH₃ | 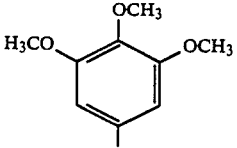 (3,4,5-trimethoxyphenyl) | —(CH₂)₃OCOCH₃ |
| 95 | CH₃ | CH₃ | 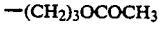 (2-Cl-C₆H₄) | —CH₂CHCH₂OSO₂CH₃<br>$\quad\;\;$ |<br>$\quad\;\;$ OSO₂CH₃ |
| 96 | CH₃ | CH₃ | 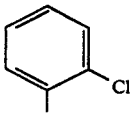 (2-Cl-C₆H₄) | —CH₂CHCH₂N(morpholino)<br>$\quad\;\;$ |<br>$\quad\;\;$ N(morpholino) |
| 97 | CH₃ | CH₃ | 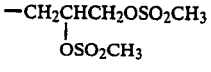 (2-Cl-C₆H₄) | —CH₂CHCH₂N(2,6-dimethylmorpholino)<br>$\quad\;\;$ |<br>$\quad\;\;$ N(2,6-dimethylmorpholino) |
| 98 | CH₃ | CH₃ | 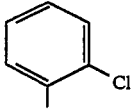 (2-Cl-C₆H₄) | —CH₂CHCH₂N(C₂H₅)₂<br>$\quad\;\;$ |<br>$\quad\;\;$ N(C₂H₅)₂ |
| 99 | CH₃ | CH₃ | 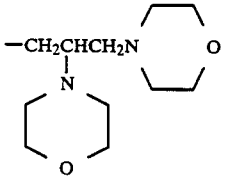 (2-Cl-C₆H₄) | —CH₂CHCH₂N(CH₃)(CH(CH₃)₂)<br>$\quad\;\;$ |<br>$\quad\;\;$ N(CH₃)(CH(CH₃)₂) |
| 100 | CH₃ | CH₃ | 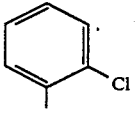 (2-Cl-C₆H₄) | —CH₂CHCH₂N(phthalimido)<br>$\quad\;\;$ |<br>$\quad\;\;$ N(phthalimido) |
| 101 | CH₃ | CH₃ | 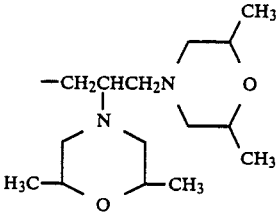 (2-Cl-C₆H₄) | —CH₂CHCH₂NH₂<br>$\quad\;\;$ |<br>$\quad\;\;$ NH₂ |

-continued

| No. | $R^1$ | $R^2$ | $R^3$ | $R^4$ |
|---|---|---|---|---|
| 102 | $CH_3$ | $CH_3$ | 2-Cl-phenyl | $-CH_2CH(NHCOCH_3)CH_2NHCOCH_3$ |
| 103 | $CH_3$ | $CH_3$ | 2-Cl-phenyl | $-CH_2CH(OCOCH_3)CH_2N(morpholino)$ |
| 104 | $CH_3$ | $CH_3$ | 2-Cl-phenyl | $-CH_2CH(OH)CH_2N(morpholino)$ |
| 105 | $CH_3$ | $CH_3$ | 2-Cl-phenyl | $-CH_2CH(CH_2OCOCH_3)N(morpholino)$ |
| 106 | $CH_3$ | $CH_3$ | 2-Cl-phenyl | $-CH_2CH(CH_2OH)N(morpholino)$ |
| 107 | $CH_3$ | $CH_3$ | 2-Cl-phenyl | $-CH_2CH(OCOCH_3)CH_2N(C_2H_5)_2$ |
| 108 | $CH_3$ | $CH_3$ | 2-Cl-phenyl | $-CH_2CH(OH)CH_2N(C_2H_5)_2$ |
| 109 | $CH_3$ | $CH_3$ | 2-Cl-phenyl | $-CONHCH_2CON(morpholino)$ |
| 110 | $CH_3$ | $CH_3$ | 2-Cl-phenyl | $-CH_2CONHCH_2CON(morpholino)$ |
| 111 | cyclopropyl | $CH_3$ | 2-Cl-phenyl | $-CONHCH(CH_3)CON(pyrrolidino)$ |
| 112 | $CH_3$ | $CH_3$ | 2-Cl-phenyl | $-CONHCH_2COOC_2H_5$ |

| No. | R¹ | R² | R³ | R⁴ |
|---|---|---|---|---|
| 113 | CH₃ | CH₃ | 2-Cl-phenyl (with additional substituent) | —CONHCH₂CH₂CON(morpholine) |
| 114 | CH₃ | CH₃ | 2-Cl-phenyl | —CONHCH₂CONH₂ |
| 115 | CH₃ | CH₃ | 2-Cl-phenyl | —CON(CH₃)CH₂CON(morpholine) |
| 116 | Br | CH₃ | 2-Cl-phenyl | —CONHCH₂CON(morpholine) |
| 117 | CH₃O | CH₃ | 2-Cl-phenyl | —CONHCH₂CON(morpholine) |
| 118 | CH₃ | CH₃ | 2-Cl-phenyl | —CONHCH(CH₂CH₂SO₂CH₃)CON(morpholine) |
| 119 | CH₃ | CH₃ | 2-Cl-phenyl | —CH₂CH₂CONHCH₂CON(morpholine) |
| 120 | CH₃ | CH₃ | 2-Cl-phenyl | —CONH—(pyrrolidinone) |
| 121 | CH₃ | CH₃ | 2-Cl-phenyl | —CONHCH(CH₂CH₂SCH₃)COOCH₃ |
| 122 | CH₃ | CH₃ | 2-Cl-phenyl | —CONHCH(CH₂COOCH₃)COOCH₃ |
| 123 | CH₃ | CH₃ | 2-Cl-phenyl | —CO(NHCH₂CO)₂—N(morpholine) |

-continued
| No. | R¹ | R² | R³ | R⁴ |
|---|---|---|---|---|
| 124 | CH₃ | CH₃ | 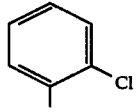 | —CONHCH₂CH₂COOCH₃ |
| 125 | CH₃ | CH₃ | 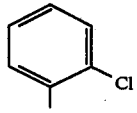 | —CONHCH₂CON(C₂H₅)₂ |
| 126 | CH₃ | CH₃ | 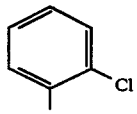 | 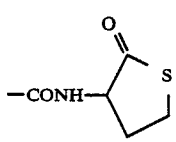 |
| 127 | CH₃ | CH₃ | 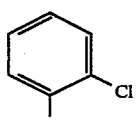 |  |
| 128 | CH₃ | CH₃ | 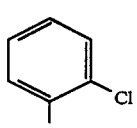 |  |
| 129 | CH₃ | CH₃ | 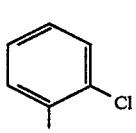 | —CONHCHCON(C₂H₅)₂<br>        CH₂CH(CH₃)₂ |
| 130 | CH₃ | CH₃ | 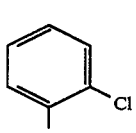 | —CONHCHCON(C₂H₅)₂<br>        CH₂CH₂SCH₃ |
| 131 | CH₃ | CH₃ | 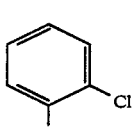 | 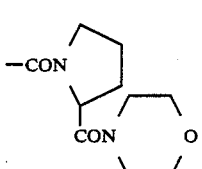 |
| 132 | CH₃ | CH₃ | 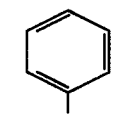 |  |
| 133 | CH₃ | CH₃ | 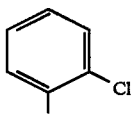 | —CONHCHCOOCH₃<br>      CH₂CH(CH₃)₂ |
| 134 | CH₃ | CH₃ | 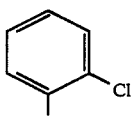 | 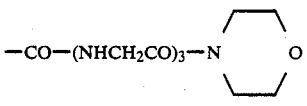 |

-continued

| No. | R¹ | R² | R³ | R⁴ |
|---|---|---|---|---|
| 135 | CH₃ | CH₃ | 2-Cl-C₆H₄ | —CONHCH₂COO(CH₃)₂N(C₂H₅)₂ |
| 136 | CH₃ | CH₃ | 2-Cl-C₆H₄ | —CONHCHCONHCH(CH₃)₂ <br>           CH(CH₃)₂ |
| 137 | CH₃ | CH₃ | 2-Cl-C₆H₄ | —CONHCHCON(piperazine)N—CH₃ <br>           CHC(CH₃)₂ |
| 138 | CH₃ | CH₃ | 2-Cl-C₆H₄ | —CONHCH₂CON(CH₃)₂ |
| 139 | CH₃ | CH₃ | 2-Cl-C₆H₄ | —CONHCHCON(morpholine) <br>           CH₂CH(CH₃)₂ |
| 140 | CH₃ | CH₃ | 2-Cl-C₆H₄ | —CONHCH₂CONH(CH₂)₂N(C₂H₅)₂ |
| 141 | CH₃ | CH₃ | 2-Cl-C₆H₄ | —CONHCHCON(morpholine) <br>           CH₂CH₂SCH₃ |
| 142 | CH₃ | CH₃ | 2-Cl-C₆H₄ | —CONHCHCONHCH₃ <br>           CH₂CH₂SCH₃ |
| 143 | H | CH₃ | 2-Cl-C₆H₄ | —CONHCH₂CON(morpholine) |
| 144 | CH₃ | CH₃ | 2-Cl-C₆H₄ | —(CONHCH₂)₂—CH=CH₂ |
| 145 | CH₃ | CH₃ | 2-Cl-C₆H₄ | —(CH₂)₂CONHCH₂COOC₂H₅ |

| No. | R¹ | R² | R³ | R⁴ |
|---|---|---|---|---|
| 146 | CH₃ | CH₃ | 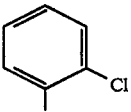 2-Cl-C₆H₄ | —CONHCH₂COOC₂H₅ |
| 147 | CH₃ | CH₃ | 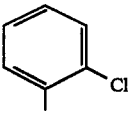 2-Cl-C₆H₄ | —CH₂CONHCH₂COOC₂H₅ |
| 148 | CH₃ | CH₃ | 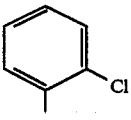 2-Cl-C₆H₄ | —CONHCH₂COOCH₃ |
| 149 | CH₃ | CH₃ | 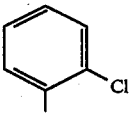 2-Cl-C₆H₄ | —CON(CH₃)CH₂COOCH₃ |
| 150 | CH₃ | CH₃ | 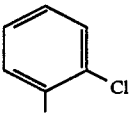 2-Cl-C₆H₄ | —CONHCH(CH₃)CONHCH₃ |
| 151 | CH₃ | CH₃ | 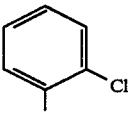 2-Cl-C₆H₄ | —(CH₂)₂OCOCH₃ |
| 152 | CH₃ | CH₃ | 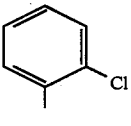 2-Cl-C₆H₄ | —(CH₂)₂OSO₂CH₃ |
| 153 | CH₃ | CH₃ | 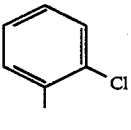 2-Cl-C₆H₄ | —(CH₂)₂N(morpholino)  |
| 154 | CH₃ | CH₃ | 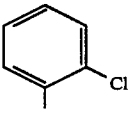 2-Cl-C₆H₄ | —(CH₂)₂N(4-methylpiperazino)  |
| 155 | CH₃ | CH₃ | 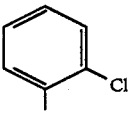 2-Cl-C₆H₄ | —(CH₂)₂N(C₂H₅)₂ |
| 156 | CH₃ | CH₃ | 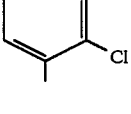 2-Cl-C₆H₄ | —(CH₂)₂NH₂ |

-continued

| No. | R¹ | R² | R³ | R⁴ |
|---|---|---|---|---|
| 157 | CH₃ | CH₃ | 2-Cl-C₆H₄ | —(CH₂)₂NHCOCH₃ |
| 158 | CH₃ | CH₃ | 2-Cl-C₆H₄ | —(CH₂)₂NHCOCH(CH₃)CH₃ |
| 159 | CH₃ | CH₃ | 2-Cl-C₆H₄ | —(CH₂)₂OH |
| 160 | CH₃ | CH₃ | 2-Cl-C₆H₄ | —(CH₂)₂CON(morpholino) |
| 161 | CH₃ | CH₃ | 2-Cl-C₆H₄ | —(CH₂)₂CON(piperidino) |
| 162 | CH₃ | CH₃ | 2-Cl-C₆H₄ | —(CH₂)₂CON(C₃H₇)₂ |
| 163 | CH₃ | CH₃ | 2-Cl-C₆H₄ | —CH₂CON(morpholino) |
| 164 | CH₃ | CH₃ | 2-Cl-C₆H₄ | —CH₂N(piperidino) |
| 165 | CH₃ | C₂H₅ | 2-Cl-C₆H₄ | —(CH₂)₂CON(morpholino) |
| 166 | CH₃ | C₂H₅ | 2-Cl-C₆H₄ | —CH₂CON(morpholino) |
| 167 | CH₃ | C₂H₅ | 2-Cl-C₆H₄ | —(CH₂)₂CONHCH(CH₃)₂ |

-continued

| No. | R¹ | R² | R³ | R⁴ |
|---|---|---|---|---|
| 168 | CH₃ | C₂H₅ | 2-Cl-C₆H₄ | —(CH₂)₂CON(CH₃)₂ |
| 169 | CH₃ | C₂H₅ | 2-Cl-C₆H₄ | —(CH₂)₂CON(pyrrolidinyl) |
| 170 | CH₃ | C₂H₅ | 2-Cl-C₆H₄ | —(CH₂)₂CON(4-methylpiperazinyl) |
| 171 | CH₃ | C₂H₅ | 2-Cl-C₆H₄ | —(CH₂)₂CON(thiomorpholinyl) |
| 172 | CH₃ | C₂H₅ | 2-Cl-C₆H₄ | —(CH₂)₂CONH₂ |
| 173 | CH₃ | C₂H₅ | 2-Cl-C₆H₄ | —(CH₂)₂CON(thiazolidinyl) |
| 174 | CH₃ | C₂H₅ | 2-CH₃-C₆H₄ | —(CH₂)₂CON(morpholinyl) |
| 175 | CH₃ | C₂H₅ | 2-OCH₃-C₆H₄ | —(CH₂)₂CON(morpholinyl) |
| 176 | CH₃ | C₂H₅ | 2-Cl-C₆H₄ | —(CH₂)₃CON(morpholinyl) |
| 177 | CH₃ | C₂H₅ | 2-Cl-C₆H₄ | —(CH₂)₄N(morpholinyl) |
| 178 | CH₃ | C₂H₅ | 2-Cl-C₆H₄ | —(CH₂)₃CON(C₂H₅)₂ |

-continued

| No. | R¹ | R² | R³ | R⁴ |
|---|---|---|---|---|
| 179 | C₂H₅ | CH₃ | 2-Cl-C₆H₄ | —(CH₂)₂CON(morpholino) |
| 180 | H | CH₃ | 2-Cl-C₆H₄ | —(CH₂)₂CON(morpholino) |
| 181 | cyclopropyl | CH₃ | 2-Cl-C₆H₄ | —(CH₂)₂CON(morpholino) |
| 182 | CH₃ | CH₃ | 2-CH₃-C₆H₄ | —CH₂CON(morpholino) |
| 183 | CH₃ | CH₃ | 2-OCH₃-C₆H₄ | —CH₂CON(morpholino) |
| 184 | CH₃ | CH₃ | 2-Cl-C₆H₄ | —CH₂CONH₂ |
| 185 | CH₃ | CH₃ | 2-Cl-C₆H₄ | —(CH₂)₂CONHCH₃ |
| 186 | CH₃ | CH₃ | 2-Cl-C₆H₄ | —(CH₂)₂CON(CH₂CH=CH₂)₂ |
| 187 | CH₃ | CH₃ | 2-Cl-C₆H₄ | —CH₂CON(pyrrolidino) |
| 188 | CH₃ | C₂H₅ | 2-Cl-C₆H₄ | —CH₂CON(pyrrolidino) |
| 189 | CH₃ | CH₃ | 2-CH₃-C₆H₄ | —CH₂CON(pyrrolidino) |

-continued

| No. | R¹ | R² | R³ | R⁴ |
|---|---|---|---|---|
| 190 | $CH_3$ | $CH_3$ | 2-methoxyphenyl | $-CH_2CON\langle pyrrolidine \rangle$ |
| 191 | $CH_3$ | $CH_3$ | 2-methoxyphenyl | $-(CH_2)_3CON\langle thiomorpholine \rangle$ |
| 192 | $CH_3$ | $CH_3$ | 2-methylphenyl | $-(CH_2)_3CON\langle thiomorpholine \rangle$ |
| 193 | $CH_3$ | $CH_3$ | 2-chlorophenyl | $-(CH_2)_3CON\langle thiomorpholine \rangle$ |
| 194 | $CH_3$ | $CH_3$ | 2-chlorophenyl | $-(CH_2)_2CONH(CH_2)_2$-phenyl |
| 195 | $CH_3$ | $CH_3$ | 2-chlorophenyl | $-(CH_2)_2CONHCH_2$-phenyl |
| 196 | $CH_3$ | $CH_3$ | 2-chlorophenyl | $-(CH_2)_3CONH_2$ |
| 197 | $CH_3$ | $C_2H_5$ | 2-chlorophenyl | $-(CH_2)_2CON\langle piperidine \rangle$ |
| 198 | $CH_3$ | $CH_3$ | 2-chlorophenyl | $-(CH_2)_2CON\langle piperazine \rangle N-CH_2CH(CH_3)_2$ |
| 199 | $CH_3$ | $CH_3$ | 2-chlorophenyl | $-(CH_2)_4CONH_2$ |
| 200 | $CH_3$ | $CH_3$ | 2-chlorophenyl | $-(CH_2)_3CON\langle piperidine \rangle$ |

-continued

| No. | R¹ | R² | R³ | R⁴ |
|---|---|---|---|---|
| 201 | CH₃ | CH₃ | 2-Cl-C₆H₄ | —(CH₂)₄CON(piperidine) |
| 202 | CH₃ | CH₃ | 2-Cl-C₆H₄ | —(CH₂)₃CON(morpholine) |
| 203 | CH₃ | CH₃ | 2-Cl-C₆H₄ | —(CH₂)₄CON(morpholine) |

| No. | R¹ | R² | R³ | R⁴ |
|---|---|---|---|---|
| 204 | CH₃ | CH₃ | 2-Cl-C₆H₄ | —CH₂N(morpholine) |
| 205 | CH₃ | CH₃ | 2-Cl-C₆H₄ | —CH₂OSO₂CH₃ |
| 206 | CH₃ | CH₃ | 2-Cl-C₆H₄ | —CH₂OH |
| 207 | CH₃ | CH₃ | 2-Cl-C₆H₄ | —CON(morpholine) |
| 208 | CH₃ | CH₃ | 2-Cl-C₆H₄ | —CON(thiomorpholine) |
| 209 | CH₃ | CH₃ | 2-Cl-C₆H₄ | —CON(pyrrolidine) |
| 210 | CH₃ | CH₃ | 2-Cl-C₆H₄ | —CON(N-methylpiperazine) |

-continued

| No. | $R^1$ | $R^2$ | $R^3$ | $R^4$ |
| --- | --- | --- | --- | --- |
| 211 | CH₃ | CH₃ | (2-chlorophenyl) | —CON(morpholino) |

Note: structure shown is the tetracyclic thieno-triazolo-diazepine with substituents $R^1$, $R^2$, $R^3$, $R^4$.

In order to determine PAF-antagonistic activity of the compounds of the present invention, the inhibitory effects of PAF-induced lethal shock in mice were investigated by oral administration and intravenous administration.

The test compounds employed are as follows:

Compound A: 3-[4-(2-chlorophenyl)-6,9-dimethyl-6H-thieno[3,2-f][1,2,4]triazolo[4,3-a][1,4]diazepin-2-yl]propionic acid morpholide Compound B: 5-(2-chlorophenyl)-3,4-dihydro-7,10-dimethyl-3-morpholinocarbonyl-2H,7H-cyclopenta[4,5]thieno[3,2-f][1,2,4]triazolo[4,3-a][1,4]diazepine Compound C: 5-(2-chlorophenyl)-3,4-dihydro-7,10-dimethyl-3-morpholinomethyl-2H,7H-cyclopenta[4,5]thieno[3,2-f][1,2,4]triazolo[4,3-a][1,4]diazepine ½ hydrate Compound D: 3-[4-(2-chlorophenyl)-6,9-dimethyl-6H-thieno[3,2-f][1,2,4]triazolo[4,3-a][1,4]diazepin-2-yl]propionic acid 4-isobutyl-1-piperazide Compound E: 3-[4-(2-chlorophenyl)-6,9-dimethyl-6H-thieno[3,2-f][1,2,4]triazolo[4,3-a][1,4]diazepin-2-yl]propionic acid N,N-dipropylamide The following compound was employed as a comparison compound.

WEB 2086: 3-[4-(2-chlorophenyl)-9-methyl-6H-thieno[3,2-f][1,2,4]triazolo[4,3-a][1,4]diazepin-2-yl]propionic acid morpholide Experiment 1: Effect on PAF-induced lethal shock in mice (p.o.)

The experiment was carried out according to the method of Young et al. described in Prostaglandins, vol. 30, p. 545 (1985). Groups of 9 to 15 male ICR mice (Charles River) weighing 25–30 g were used. 80 μg/kg of PAF (Serdary Research Lab.) solution was intravenously administered in a lateral tail vein 1 hour after the oral administration of test compound (0.1 ml/10 g). All animals were observed for 24 hours after the PAF injection. Results were given as ED₅₀ (mg/kg) in Table 1.

TABLE 1

| Compound | $ED_{50}$ (mg/kg, p.o.) |
| --- | --- |
| A | 0.065 |
| B | 0.55 |
| C | 0.2 |
| D | 0.3 |
| E | 0.14 |
| WEB 2086 | 1.6 |

Experiment 2: Effect on PAF-induced lethal shock in mice (i.v.)

The experiment was carried out according to the method of Young et al. as described in Experiment 1. Groups of 8 to 15 male ICR mice (Charles River) weighing 25–30 g were used. 80 μg/kg of PAF (Serdary Research Lab.) solution was intravenously administered in a lateral a tail vein 1 hour after the intravenous administration of test compound (0.1 mg/10 g). All animals were observed for 24 hours after the PAF injection. Results were given as ED₅₀ (mg/kg) in Table 2.

TABLE 2

| Compound | $ED_{50}$ (mg/kg, i.v.) |
| --- | --- |
| A | 0.021 |
| WEB 2086 | 0.125 |

The acute toxicity of the compounds of the present invention was studied in 6 male mice. The mice were observed for 5 days after the oral administration of the compound. All mice survived at the dose of 1000 mg/kg of the compounds.

It becomes clear from the results of the various pharmacological experiments inclusive of those mentioned above that the compounds of the present invention exhibit potent and long-lasting PAF-antagonistic activity, and that such superior activity is also observed by the oral administration, and further, the PAF-antagonistic activity of the compounds of the present invention is far more potent than that of WEB 2086 in oral administration.

Moreover, the compounds of the present invention have less affinity for the benzodiazepine receptor and exhibit no depressive effects on the central system such as sedative or muscle relaxation activity.

In view of the above facts, the compounds of the present invention are useful as PAF-antagonists, and are preventable or treatable various kinds of PAF-induced diseases such as inflammatory diseases, allergic diseases, anaphylactic shocks, septic shocks, myocardiac diseases, asthma, pulmonary edema or adult respiratory diseases.

The compounds (I) of the present invention and pharmaceutically acceptable acid addition salts thereof can be safely administered orally or parenterally in human beings in the form of a pharmaceutical composition such as tablets, pills, powder, capsules, granules, solutions, inhalants, suppositories, percutaneous absorption preparations or injectable solutions. The pharmaceutical composition can be prepared by, for example, mixing a therapeutically effective amount of at least one compound with a pharmaceutically acceptable additives such as an excipient, an extender, a diluent or a solubilizer.

The dose may vary depending upon the compound selected or employed, the severity of the patients to be treated or the age of the patients, but the daily dose for human adults preferably ranges from 0.1 to 100 mg in single or multiple dose.

The present invention will be explained by the following reference examples and examples in more detail, but these examples are not to be construed as limiting the present invention.

REFERENCE EXAMPLE 1

7-(3-Acetoxypropyl)-5-(2-chlorophenyl)-3-methyl-1,3-dihydro-2H-thieno[2,3-e]-1,4-diazepine-2-thione.

(a) To a mixture of 35.9 g of 2-chlorocyanoacetophenone, 6.7 g of sulfur and 21.5 g of 5-hydroxyvaleraldehyde in 50 ml of dimethylformamide is added 21.2 g of triethylamine with stirring and then stirred at 60° C. for 3 hours. The mixture is poured into ice-cold water and the organic layer is extracted with 300 ml of toluene The extract is washed with water and dried over anhydrous magnesium sulfate. After separating by filtration, the filtrate is concentrated under reduced pressure to give 60.5 g of 2-amino-3-(2-chlorobenzoyl)-5-(3-hydroxypropyl)-thiophene as crude oil.

NMR (CDCl$_3$), δ(ppm): 7.2–7.6 (4H, m), 6.14 (1H, s), 3.69 (2H, t), 2.88 (2H, t), 1.88 (2H, m).

(b) To a solution of 30 g of the above-mentioned compound in 200 ml of ethyl acetate is saturated with dry gas of hydrogen chloride and then stirred at room temperature for 4 hours. The solvent is concentrated under reduced pressure and the residue is dissolved in 200 ml of chloroform. The solution is washed with 5% aqueous sodium hydrogencarbonate solution and water and dried over anhydrous magnesium sulfate. After separating by filtration, the filtrate is concentrated under reduced pressure and the resulting oil is subjected to column chromatography on silica gel to give 25 g of 2-amino-5-(3-acetoxypropyl)-3-(2-chlorobenzoyl)thiophene.

NMR (CDCl$_3$), δ(ppm): 7.2–7.6 (4H, m), 7.09 (2H, broad), 6.13 (1H, s), 4.07 (2H, t), 2.61 (2H, t), 2.02 (3H, s), 1.85 (2H, m).

MS (z/m)=323.

(c) To a solution of 25 g of compound obtained by (b) is added 20.2 g of N-phthalylalanylchloride and then refluxed under heating with stirring for 2 hours. After cooling, the mixture is washed with 5% aqueous sodium hydrogencarbonate solution and water and then dried over anhydrous magnesium sulfate. After separating by filtration, the filtrate is concentrated under reduced pressure to give 40 g of 5-(3-acetoxypropyl)-3-(2-chlorobenzoyl)-2-(N-phthalylalanyl)aminothiophene.

NMR (CDCl$_3$), δ(ppm): 7.6–8.0 (4H, m), 6.9–7.1 (4H, m), 6.33 (1H, s), 5.28 (1H, q), 4.06 (2H, t), 2.61 (2H, t), 2.02 (3H, s), 1.98 (3H, d), 1.85 (2H, m), 1.84 (2H, m), 1.42 (3H, d). MS (z/m)=538.

(d) To a suspension of 30 g of compound obtained in above (c) in 300 ml of methanol is added 7.7 g of methylhydrazine under ice-cooling with stirring and then stirred at room temperature for 3 hours. To the mixture is added 17 ml of concentrated hydrochloric acid and stirred at 50°–60° C. for 2 hours. The mixture is concentrated under reduced pressure and the residue is dissolved in 150 ml of chloroform. The solution is washed with 5% aqueous sodium hydrogencarbonate solution and water and then dried over anhydrous magnesium sulfate. After separating by filtration, the filtrate is concentrated under reduced pressure to give 22 g of 2-N-alanylamino-5-(3-acetoxypropyl)-3-(2-chlorobenzoyl)-thiophene as oil.

NMR (CDCl$_3$), δ(ppm): 6.9–7.1 (4H, m), 6.25 (1H, s), 3.72 (1H, q), 4.06 (2H, t), 2.61 (2H, t), 2.03 (3H, s), 1.84 (2H, m), 1.42 (3H, t).

MS (z/m)=408.

(e) To a solution of 22 g of compound obtained in above (d) in 500 ml of toluene is added 100 g of silica gel and refluxed under heating with stirring for 5 hours. After cooling, the silica gel is collected by filtration and extracted with heated methanol is distilled off and the residue is subjected to chromatography on silica gel to give 11 g of 7-(3-acetoxypropyl)-5-(2-chlorophenyl)-3-methyl-1,3-dihydro-2H-thieno[2,3-e]-1,4-diazepin-2-one as colorless crystals.

NMR (CDCl$_3$), δ(ppm): 6.9–7.1 (4H, m), 6.21 (1H, s), 4.06 (2H, t), 3.98 (1H, q), 2.62 (2H, t), 2.03 (3H, s), 1.84 (2H, m), 1.82 (3H, d).

(f) To a solution of 10 g of compound obtained in above (e) in 100 ml of chloroform is added 2.6 g of phosphorus pentasulfide and refluxed under heating with stirring for 5 hours. After cooling, the mixture is washed with 5% aqueous sodium hydrogencarbonate solution and water and then dried over anhydrous magnesium sulfate After separating by filtration, the filtrate is concentrated under reduced pressure to give 10 g of 7-(3-acetoxypropyl)-5-(2-chlorophenyl)-3-methyl-1,3-dihydro-2H-thieno[2,3-e]-1,4-diazepine-2-thione.

NMR (CDCl$_3$), δ(ppm): 6.9–7.1 (4H, m), 6.20 (1H, s), 4.16 (1H, q), 4.06 (2H, t), 2.62 (2H, t), 2.03 (3H, s), 1.94 (3H, d), 1.84 (2H, m).

EXAMPLE 1

To a suspension of 6 g of 7-(3-acetoxypropyl)-5-(2-chlorophenyl)-3-methyl-1,3-dihydro-2H-thieno[2,3-e]-1,4-diazepine-2-thione obtained in Reference example 1 in 60 ml of methanol is added 2.2 g of 100% hydrazine monohydrate with stirring under ice-cooling and stirred at room temperature for 2 hours. The methanol is distilled off under reduced pressure and the residue is dissolved in 100 ml of chloroform. The solution is washed with water and then dried over anhydrous magnesium sulfate. After separating by filtration, the filtrate is concentrated under reduced pressure and the resulting oily hydrazino compound is dissolved in 100 ml of toluene. To the solution is added 4.8 g of ethyl orthoacetate and refluxed under heating for 2 hours. The mixture is concentrated under reduced pressure and the residue is subjected to chromatography on silica gel to produce 3 g of 2-(3-acetoxypropyl)-4-(2-chlorophenyl)-6,9-dimethyl-6H-thieno[3,2-f][1,2,4]triazolo[4,3-a][1,4]diazepine as colorless crystals.

NMR (CDCl$_3$), δ(ppm): 6.9–7.1 (4H, m), 6.34 (1H, s), 4.32 (1H, q), 4.06 (2H, t), 2.62 (2H, t), 2.72 (3H, s), 2.03 (3H, s), 1.84 (2H, m).

EXAMPLE 2

To a solution of 2 g of compound obtained in Example 1 in 40 ml of methanol is added one equivalent of 2 normal sodium hydroxide solution and stirred at room temperature for 2 hours. The methanol is distilled off under reduced pressure and the residue is dissolved in 50 ml of chloroform. The solution is washed with water and then dried over anhydrous magnesium sulfate. After separating by filtration, the filtrate is concentrated under reduced pressure to give 1.7 g of 4-(2-chlorophenyl)-2-(3-hydroxypropyl)-6,9-dimethyl-6H-thieno[3,2-f][1,2,4]triazolo[4,3-a][1,4]diazepine.

NMR (CDCl$_3$), δ(ppm): 7.2–7.6 (4H, m), 6.48 (1H), 4.42 (1H, q), 3.66 (2H, t), 2.88 (2H, t), 2.67 (3H, s), 2.10 (3H, d), 1.60–2.0 (2H, m).

The following compounds can be prepared in similar manners as the above Examples.

EXAMPLE 3

4-(2-chlorophenyl)-2-(2-hydroxyethyl)-6,9-dimethyl-6H-thieno[3,2-f][1,2,4]triazolo[4,3-a][1,4]diazepine, melting at 151°–153° C.

NMR (CDCl$_3$), δ(ppm): 7.2–7.6 (4H, m), 6.44 (1H), 4.34 (1H), 3.84 (2H, t), 3.0 (2H, t), 2.68 (3H, t), 2.08 (3H, d).

EXAMPLE 4

5-(2-chlorophenyl)-3,4-dihydro-7,10-dimethyl-3-morpholinomethyl-2H,7H-cyclopenta[4,5]thieno[3,2-f][1,2,4]triazolo[4,3-a][1,4]diazepine ¼ hydrate, melting at 126°–132° C.

NMR (CDCl$_3$), δ(ppm): 7.2–7.6 (4H, m), 4.32 (1H, q), 2.70 (3H, s), 2.12 (3H, d), 1.4–3.8 (15H, m) MS (m/z)=467.

EXAMPLE 5

5-(2-chlorophenyl)-3,4-dihydro-7,10-dimethyl-3-methylsulfonyloxymethyl-2H,7H-cyclopenta[4,5]-thieno[3,2-f][1,2,4]triazolo[4,3-a][1,4]diazepine.

NMR (CDCl$_3$), δ(ppm): 7.2–7.6 (4H, m), 4.32 (1H, q), 4.08–4.10 (2H, m), 3.0 (3H, d), 3.72 (3H, s), 2.12 (3H, d), 1.4–3.4 (5H, m).

MS (m/z)=476.

EXAMPLE 6

5-(2-chlorophenyl)-3,4-dihydro-3-hydroxymethyl-7,10-dimethyl-2H,7H-cyclopenta[4,5]thieno[3,2-f][1,2,4]triazolo[4,3-a][1,4]diazepine.

NMR (CDCl$_3$), δ(ppm): 7.2–7.6 (4H, m), 4.34 (1H, q), 3.4–3.7 (2H, m), 2.68 (3H, s), 2.12 (3H, d), 1.4–3.4 (5H, m).

MS (m/z)=398.

REFERENCE EXAMPLE 2

To a suspension of 53.5 g of 2-chlorocyanoacetophenone and 9.5 g of sulfur in 120 ml of dimethylformamide is added 71 g of dicarboethoxybutylaldehyde under ice-cooling with stirring. To the mixture is added 30 g of triethylamine and stirred at 60°–70° C. for 3 hours. The mixture is poured into ice-cold water and extracted with 1 l of ethyl acetate, and the extract is washed with water and dried over anhydrous magnesium sulfate After separating by filtration, the filtrate is concentrated under reduced pressure and the residue is crystallized from a mixture of isopropyl alcohol-water (7:3) to give 78 g of diethyl 2-[[5-amino-4-(2-chlorobenzoyl)-2-thienyl]methyl]malonate.

To a solution of 58 g of above compound in 350 ml of ethanol is added a solution of 23 g of potassium hydroxide in 90 ml of water and refluxed under heating with stirring for 2 hours. After cooling, the mixture is concentrated under reduced pressure to eliminate ethanol and to the residue is added 100 ml of water. The solution is acidified with hydrochloric acid and the organic layer is extracted with 500 ml of ethyl acetate. The extract is washed with water and dried over anhydrous magnesium sulfate. After separating by filtration, the filtrate is concentrated under reduced pressure and the residue is crystallized from toluene to give 50 g of 2-[[5-amino-4-(2-chlorobenzoyl)-2-thienyl]methyl]malonic acid as yellow crystals, melting at 150°–160° C. with decomposition.

To a solution of 50 g of above malonic acid derivative in 100 ml of dimethylformamide is added 240 ml of toluene and stirred at 80°–90° C. for 2 hours. After cooling, the mixture is concentrated under reduced pressure and the residue is crystallized from toluene to give 36.5 g of 3-[5-amino-4-(2-chlorobenzoyl)-2-thienyl]propionic acid as yellow crystals, melting at 170°–173° C.

To a solution of 47.5 g of above propionic acid derivative in 900 ml of methanol is added 0.9 ml of concentrated sulfuric acid and stirred at 20° C. for 17 hours. After the mixture is concentrated under reduced pressure, the residue is dissolved in 200 ml of water and the organic layer is extracted with 600 ml of ethyl acetate. The extract is washed with 5% potassium carbonate solution and sodium chloride solution and dried over anhydrous magnesium sulfate. After separating by filtration, the filtrate is concentrated under reduced pressure and the residue is crystallized from isopropyl ether to give 49 g of methyl 3-[5-amino-4-(2-chlorobenzoyl)-2-thienyl]propionate as crimson crystals, melting at 89°–90° C.

To a solution of 54 g of N-benzyloxycarbonyl-alanine in a mixture of 100 ml of dimethylformamide and 300 ml of methylene chloride is added 18 ml of thionyl chloride dropwise at −20° C. with stirring for 10 minutes and stirred at the same temperature of 1 hour. To the mixture is added 39 g of above methyl propionate derivative in 50 ml of methylene chloride dropwise for 15 minutes and stirred at the same temperature for 5 hours The mixture is poured into ice-cold water, alkalified with potassium carbonate and extracted with 400 ml of chloroform. The extract is washed with water and dried over anhydrous magnesium sulfate. After separating by filtration, the filtrate is concentrated under reduced pressure and the residue is crystallized from isopropyl ether to give 52 g of methyl 3-[5-(2-benzyloxycarbonylamino)propionylamino-4-(2-chlorobenzoyl)-2-thienyl]propionate as colorless crystals, melting at 125°–127° C.

To a suspension of 52 g of the above compound in 60 ml of acetic acid are added 5 ml of anisole and 40 ml of 30% hydrobromic acid-acetic acid solution and stirred at 20° C. for 2 hours. The mixture is poured into ice-cold water, alkalified with potassium carbonate and extracted with 400 ml of ethyl acetate. The extract is washed with sodium chloride solution and dried over anhydrous magnesium sulfate. After separating by filtration, the filtrate is concentrated under reduced pressure, the residue is washed with isopropyl ether and dissolved in 650 ml of toluene. To the solution is added 100 g of silica gel and refluxed under heating with a water separator for 4 hours. After cooling, silica gel is collected by filtration and extracted with 200 ml of hot methanol. The methanol is concentrated under reduced pressure, the residue is subjected to chromatography on silica gel and eluted with a mixture of chloroform-methanol (100:1 to 100:3). The eluate of the objective fraction is concentrated under reduced pressure and the residue is crystallized from isopropyl ether to give 9.5 g of methyl 3-[5-(2-chlorophenyl)-2,3-dihydro-3-methyl-2-oxo-1H-thieno[2,3-e]-1,4-diazepin-7-yl]propionate as colorless crystals, melting at 196°–197° C.

To a solution of 8.4 g of above thienodiazepine derivative in 80 ml of diethylene glycol dimethyl ether are added 10 g of phosphorus pentasulfide and 7.5 g of sodium hydrogencarbonate and then stirred at 60° C. for 3.5 hours. The mixture is poured into ice-cold water with stirring, stirred for 40 minutes, and the precipitated crystals are collected by filtration and then washed with water. The crystals are dried, subjected to chromatography on silica gel and eluted with a mixture of chloroform-methanol (100:1 to 100:2). The eluate of the objective fraction is concentrated under reduced pressure and the residue is crystallized from isopropyl ether to give 5.3 g of methyl 3-[5-(2-chlorophenyl)-2,3-dihydro-3-methyl-2-thioxo-1H-thieno[2,3-e]-1,4-diazepin-7-yl]propionate as yellow crystals, melting at 198°-200° C.

To a solution of 3.2 g of the above compound in 50 ml of tetrahydrofuran is added 600 mg of 100% hydrazine hydrate and stirred at 40°-45° C. for 20 minutes. The mixture is concentrated under reduced pressure and the residue is dissolved in 80 ml of toluene To the solution is added 2.6 g of ethyl orthoacetate and stirred at 70° C. for 1.5 hours. The mixture is concentrated under reduced pressure and the residue is crystallized from a mixture of isopropyl ether-methylene chloride (1:1) to give 2.8 g of methyl 3-[4-(2-chlorophenyl)-6,9-dimethyl-6H-thieno[3,2-f][1,2,4]triazolo[4,3-a][1,4]diazepin-2-yl]propionate as colorless crystals, melting at 131°-132° C.

To a solution of 2.8 g of the above thienotriazolodiazepine compound in 30 ml of methanol is added solution of 1 g of potassium hydroxide in 8 ml of water and stirred at room temperature for 1 hour. The mixture is concentrated under reduced pressure and to the residue is added 50 ml of water. The solution is acidified with hydrochloric acid and extracted with 100 ml of chloroform. The extract is washed with water and dried over anhydrous magnesium sulfate. After separating by filtration, the filtrate is concentrated under reduced pressure and the residue is crystallized from isopropyl ether-methylene chloride (1:1) to give 2.2 g of 3-[4-(2-chlorophenyl)-6,9-dimethyl-6H-thieno[3,2-f][1,2,4]triazolo-[4,3-a][1,4]diazepin-2-yl]propionic acid as colorless crystals, melting at 202°-204° C.

REFERENCE EXAMPLE 3

To a suspension of 90 g of 2-chlorocyanoacetophenone and 16 g of sulfur in 200 ml of dimethylformamide is added 110 g of dicarboethoxypropionaldehyde under ice-cooling with stirring. To the mixture is added 51 g of triethylamine and stirred at 70° C. for 3 hours. The mixture is poured into ice-cold water and extracted with 1 l of ethyl acetate, and the extract is washed with water and dried over anhydrous magnesium sulfate. After separating by filtration, the filtrate is concentrated under reduced pressure and the residue is crystallized from a mixture of isopropyl alcohol-water (6:4) to give 100 g of diethyl 2-[5-amino-4-(2-chlorobenzoyl)-2-thienyl]malonate.

To a solution of 100 g of the above compound in 640 ml of ethanol is added a solution of 42 g of potassium hydroxide in 160 ml of water and refluxed under heating with stirring for 2 hours. After cooling, the mixture is concentrated under reduced pressure to eliminate ethanol and to the residue is added 200 ml of water. The solution is acidified with hydrochloric acid and the organic layer is extracted with 500 ml of ethyl acetate. The extract is washed with water and dried over anhydrous magnesium sulfate. After separating by filtration, the filtrate is concentrated under reduced pressure to give 90 g of 2-[5-amino-4-(2-chlorobenzoyl)-2-thienyl]-malonic acid as crude brown oil.

To a solution of above malonic acid derivative in 160 ml of dimethylformamide is added 400 ml of toluene and stirred at 80° C. for 2 hours After cooling, the mixture is concentrated under reduced pressure and the residue is crystallized from toluene to give 55 g of 2-[5-amino-4-(2-chlorobenzoyl)-2-thienyl]acetic acid as yellow crystals, melting at 172°-182° C.

To a solution of 55 g of above acetic acid derivative in 1 l of methanol is added 0.9 ml of concentrated sulfuric acid and stirred at 20° C. for 19 hours. After the mixture is concentrated under reduced pressure, the residue is dissolved in 300 ml of water and extracted with 700 ml of ethyl acetate. The extract is washed with 5% sodium hydrogencarbonate solution and water and dried over anhydrous magnesium sulfate. After separating by filtration, the filtrate is concentrated under reduced pressure and the residue is crystallized from isopropyl ether to give 47 g of methyl 2-[5-amino-4-(2-chlorobenzoyl)-2-thienyl]acetate as crimson crystals, melting at 102°-105° C.

To a solution of 29 g of N-benzyloxycarbonyl-alanine in a mixture of 40 ml of dimethylformamide and 140 ml of methylene chloride is added 9.5 ml of thionyl chloride dropwise at −20° C. with stirring for 10 minutes and stirred at the same temperature of 1 hour. To the mixture is added 20 g of above methyl acetate derivative in 30 ml of methylene chloride dropwise for 15 minutes and stirred at the same temperature for 5 hours. The mixture is poured into ice-cold water, alkalified with potassium carbonate and extracted with 300 ml of chloroform. The extract is washed with water and dried over anhydrous magnesium sulfate After separating by filtration, the filtrate is concentrated under reduced pressure to give 34 g of methyl 2-[5-(2-benzyloxycarbonylamino)propionylamino-4-(2-chlorobenzoyl)-2-thienyl]acetate as crude brown oil.

To a solution of 34 g of the above compound in 30 ml of acetic acid are added 1 ml of anisole and 40 ml of 25% hydrobromic acid-acetic acid solution and stirred at 20° C. for 3 hours. The mixture is poured into ice-cold water with stirring, alkalified with potassium carbonate and extracted with 300 ml of ethyl acetate. The extract is washed with sodium chloride solution. To the extract are added 6 ml of diethylamine and 5 g of sodium hydrogencarbonate, and stirred at 20° C. for 2 hours and then allowed to stand at the same temperature for 14 hours. The mixture is washed with water and dried over anhydrous magnesium sulfate. After separating by filtration, the filtrate is concentrated under reduced pressure and the residue is dissolved in 500 ml of toluene. To the solution is added 70 g of silica gel and refluxed under heating with a water separator for 7 hours. After cooling, silica gel is collected by filtration and extracted with 200 ml of hot methanol. The methanol is concentrated under reduced pressure, the residue is subjected to chromatography on silica gel and eluted with a mixture of chloroformmethanol (100:1 to 100:3). The eluate of the objective fraction is concentrated under reduced pressure and the residue is crystallized from isopropyl ether to give 6.9 g of methyl 2-[5-(2-chlorophenyl)-2,3-dihydro-3-methyl-2-oxo-1H-thieno[2,3-e]-1,4-diazepin-7-yl]acetate as colorless crystals, melting at 185°-190° C.

To a suspension of 6.8 g of above thienodiazepine derivative in 70 ml of diethylene glycol dimethyl ether are added 6.5 g of sodium hydrogencarbonate and 8.5 g of phosphorus pentasulfide and then stirred at 55°–60° C. for 4 hours. The mixture is poured into ice-cold water with stirring, stirred for 40 minutes, and the precipitated crystals are collected by filtration and then washed with water. The crystals are dried, subjected to chromatography on silica gel and eluted with a mixture of chloroform-methanol (100:1 to 100:2). The eluate of the objective fraction is concentrated under reduced pressure to give 3.7 g of methyl 2-[5-(2-chlorophenyl)-2,3-dihydro-3-methyl-2-thioxo-1H-thieno[2,3-e]-1,4-diazepin-7-yl]acetate as yellow crystals, melting at 196°–197° C.

To a solution of 3.7 g of the above compound in 50 ml of tetrahydrofuran is added 0.7 g of 100% hydrazine hydrate with stirring and stirred at room temperature for 30 minutes. The mixture is concentrated under reduced pressure and the residue is dissolved in 70 ml of toluene. To the solution is added 3.6 ml of ethyl orthoacetate and stirred at 80° C. for 4 hours. The mixture is concentrated under reduced pressure and the residue is crystallized from a mixture of isopropyl ether-methylene chloride (1:1) to give 3.7 g of methyl 2-[4-(2-chlorophenyl)-6,9-dimethyl-6H-thieno[3,2-f][1,2,4]triazolo[4,3-a][1,4]diazepin-2-yl]acetate as colorless crystals, melting at 105°–106° C.

To a solution of 3.7 g of the above thienotriazolodiazepine compound in 60 ml of methanol is added solution of 1.5 g of potassium hydroxide in 20 ml of water and stirred at room temperature for 1 hour. The mixture is concentrated under reduced pressure and to the residue is added 70 ml of water. The solution is acidified with hydrochloric acid and extracted with 150 ml of chloroform. The extract is washed with water and dried over anhydrous magnesium sulfate. After separating by filtration, the filtrate is concentrated under reduced pressure and the residue is crystallized from isopropyl ether to give 3.4 g of 2-[4-(2-chlorophenyl)-6,9-dimethyl-6H-thieno[3,2-f][1,2,4]triazolo[4,3-a][1,4]diazepin-2-yl]acetic acid as colorless crystals, melting at 222°–225° C.

REFERENCE EXAMPLE 4

To a solution of 29 g of α-N-benzyloxycarbonylaminobutyric acid in a mixture of 70 ml of dimethylformamide and 200 ml of methylene chloride is added 9 ml of thionyl chloride dropwise at −20° C. with stirring for 10 minutes and stirred at the same temperature of 1 hour. To the mixture is added solution of 20 g of methyl 3-[5-amino-4-(2-chlorobenzoyl)-2-thienyl]propionate obtained in Reference example 2 in 40 ml of methylene chloride dropwise for 15 minutes and stirred at the same temperature for 5 hours. The mixture is poured into ice-cold water, alkalified with potassium carbonate and extracted with 300 ml of chloroform. The extract is washed with water and dried over anhydrous magnesium sulfate. After separating by filtration, the filtrate is concentrated under reduced pressure and the residue is crystallized from isopropyl ether to give 28 g of methyl 3-[5-(2-benzyloxycarbonylamino)butyrlamino-4-(2-chlorobenzoyl)-2-thienyl]propionate as colorless crystals, melting at 106°–109° C.

To a suspension of 19 g of the above compound in 20 ml of acetic acid are added 2 ml of anisole and 20 ml of 30% hydrobromic acid-acetic acid solution and stirred at 20° C. for 2 hours. The mixture is poured into ice-cold water with stirring, alkalified with potassium carbonate and extracted with 200 ml of ethyl acetate. The extract is washed with sodium chloride solution. To the extract are added 3.6 ml of diethylamine and 3 g of sodium hydrogencarbonate, and stirred at 20° C. for 2 hours and then allowed to stand at the same temperature for 14 hours. The mixture is washed with water and dried over anhydrous magnesium sulfate. After separating by filtration, the filtrate is concentrated under reduced pressure and the residue is dissolved in 500 ml of toluene. To the solution is added 50 g of silica gel and refluxed under heating with a water separator for 7 hours. After cooling, silica gel is collected by filtration and extracted with 200 ml of hot methanol. The methanol is concentrated under reduced pressure, the residue is subjected to chromatography on silica gel and eluted with a mixture of chloroformmethanol (100:1 to 100:3). The eluate of the objective fraction is concentrated under reduced pressure and the residue is crystallized from isopropyl ether to give 4.3 g of methyl 3-[5-(2-chlorophenyl)-3-ethyl-2,3-dihydro-2-oxo-1H-thieno[2,3-e]-1,4-diazepin-7-yl]propionate as colorless crystals, melting at 187°–189° C.

To a suspension of 6.2 g of above thienodiazepine derivative in 60 ml of diethylene glycol dimethyl ether are added 5.3 g of sodium hydrogencarbonate and 7 g of phosphorus pentasulfide and then stirred at 60°–65° C. for 3 hours. The mixture is poured into ice-cold water with stirring, stirred for 40 minutes, and the precipitated crystals are collected by filtration and then washed with water. The crystals are dried, subjected to chromatography on silica gel and eluted with a mixture of chloroform-methanol (100:1 to 100:2). The eluate of the objective fraction is concentrated under reduced pressure to give 3.2 g of methyl 3-[5-(2-chlorophenyl)-2,3-dihydro-3-ethyl-2-thioxo-1H-thieno[2,3-e]-1,4-diazepin-7-yl]propionate as yellow crystals, melting at 173°–176° C.

To a solution of 3.1 g of the above compound in 50 ml of tetrahydrofuran is added 0.6 g of 100% hydrazine hydrate and stirred at 40°–45° C. for 30 minutes. The mixture is concentrated under reduced pressure and the residue is dissolved in 80 ml of toluene. To the solution is added 2.8 ml of ethyl orthoacetate and stirred at 70° C. for 4 hours. The mixture is concentrated under reduced pressure and the residue is crystallized from a mixture of isopropyl ether-methylene chloride (1:1) to give 2.7 g of methyl 3-[4-(2-chlorophenyl)-6-ethyl-9-methyl-6H-thieno[3,2-f][1,2,4]triazolo[4,3-a][1,4]diazepin-2-yl]propionate as colorless crystals, melting at 126°–127° C.

To a solution of 2.6 g of the above thienotriazolodiazepine compound in 30 ml of methanol is added solution of 1.5 g of potassium hydroxide in 10 ml of water and stirred at room temperature for 2 hours. The mixture is concentrated under reduced pressure and to the residue is added 50 ml of water. The solution is acidified with hydrochloric acid and extracted with 100 ml of chloroform. The extract is washed with water and dried over anhydrous magnesium sulfate. After separating by filtration, the filtrate is concentrated under reduced pressure and the residue is crystallized from isopropyl ether to give 2.1 g of 3-[4-(2-chlorophenyl)-6-ethyl-9-methyl-6H-thieno[3,2-f][1,2,4]triazolo[4,3-a][1,4]diazepin-2-yl]propionic acid as colorless crystals, melting at 218°–220° C.

Reference Example 5

To a solution of 28 g of α-N-benzyloxycarbonyl-aminobutyric acid in a mixture of 70 ml of dimethylformamide and 200 ml of methylene chloride is added 9 ml of thionyl chloride dropwise at −20° C. with stirring for 10 minutes and stirred at the same temperature of 1 hour. To the mixture is added solution of 18.5 g of methyl 2-[5-amino-4-(2-chlorophenyl)-2-thienyl]acetate obtained in Reference example 3 in 50 ml of methylene chloride dropwise for 15 minutes and stirred at the same temperature for 5 hours. The mixture is poured into ice-cold water with stirring, alkalified with potassium carbonate and extracted with 300 ml of chloroform. The extract is washed with water and dried over anhydrous magnesium sulfate. After separating by filtration, the filtrate is concentrated under reduced pressure to give 40 g of methyl 2-[5-(2-benzyloxycarbonylamino)-butyrylamino-4-(2-chlorobenzoyl)-2-thienyl]acetate as crude brown oil.

To a solution of 40 g of the above compound in 20 ml of acetic acid are added 2 ml of anisole and 40 ml of 25% hydrobromic acid-acetic acid solution and stirred at room temperature for 2 hours. The mixture is poured into ice-cold water with stirring, alkalified with potassium carbonate and extracted with 300 ml of ethyl acetate. The extract is washed with sodium chloride solution. To the extract are added 6 ml of diethylamine and 5 g of sodium hydrogencarbonate, and stirred at 20° C. for 4 hours and then allowed to stand at the same temperature for 14 hours. The mixture is washed with water and dried over anhydrous magnesium sulfate. After separating by filtration, the filtrate is concentrated under reduced pressure and the residue is dissolved in 500 ml of toluene. To the solution is added 70 g of silica gel and refluxed under heating with a water separator for 7.5 hours. After cooling, silica gel is collected by filtration and extracted with 200 ml of hot methanol. The methanol is concentrated under reduced pressure, the residue is subjected to chromatography on silica gel and eluted with a mixture of chloroform-methanol (100:1 to 100:3). The eluate of the objective fraction is concentrated under reduced pressure and the residue is crystallized from isopropyl ether to give 3.1 g of methyl 2-[5-(2-chlorophenyl)-3-ethyl-2,3-dihydro-2-oxo-1H-thieno[2,3-e]-1,4-diazepin-7-yl]acetate as colorless crystals, melting at 202°–204° C.

To a suspension of 3 g of above thienodiazepine derivative in 30 ml of diethylene glycol dimethyl ether are added 2.7 g of sodium hydrogencarbonate and 3.5 g of phosphorus pentasulfide and then stirred at 55°–60° C. for 4 hours. The mixture is poured into ice-cold water with stirring, stirred for 40 minutes, and the precipitated crystals are collected by filtration and then washed with water. The crystals are dried, subjected to chromatography on silica gel and eluted with a mixture of chloroform-methanol (100:1 to 100:3). The eluate of the objective fraction is concentrated under reduced pressure to give 1.5 g of methyl 2-[5-(2-chlorophenyl)-3-ethyl-2,3-dihydro-2-thioxo-1H-thieno[2,3-e]-1,4-diazepin-7-yl]acetate as yellow crystals, melting at 199°–200° C.

To a solution of 1.4 g of the above compound in 20 ml of tetrahydrofuran is added 0.27 g of 100% hydrazine hydrate and stirred at 40°–45° C. for 30 minutes. The mixture is concentrated under reduced pressure and the residue is dissolved in 30 ml of toluene. To the solution is added 1.3 ml of ethyl orthoacetate and stirred at 75° C. for 4.5 hours. The mixture is concentrated under reduced pressure and the residue is crystallized from a mixture of ethyl acetate-isopropyl ether to give 1.2 g of methyl 2-[4-(2-chlorophenyl)-6-ethyl-9-methyl-6H-thieno[3,2-f][1,2,4]triazolo[4,3-a][1,4]diazepin-2-yl]acetate as colorless crystals, melting at 134°–137° C.

To a solution of 1.2 g of the above thienotriazolodiazepine compound in 15 ml of methanol is added solution of 0.4 g of potassium hydroxide in 5 ml of water and stirred at room temperature for half an hour. The mixture is concentrated under reduced pressure and to the residue is added 50 ml of water. The solution is acidified with hydrochloric acid and extracted with 80 ml of chloroform. The extract is washed with water and dried over anhydrous magnesium sulfate. After separating by filtration, the filtrate is concentrated under reduced pressure and the residue is crystallized from isopropyl ether to give 0.9 g of 2-[4-(2-chlorophenyl)-6-ethyl-9-methyl-6H-thieno[3,2-f][1,2,4]triazolo[4,3-a][1,4]diazepin-2-yl]acetic acid as colorless crystals, melting at 170°–180° C.

The following starting compounds can be prepared in similar manners.

3-[4-phenyl-6,9-dimethyl-6H-thieno[3,2-f][1,2,4]triazolo[4,3-a][1,4]diazepin-2-yl]propionic acid, 3-[4-(2-methoxyphenyl)-6,9-dimethyl-6H-thieno[3,2-f][1,2,4]triazolo[4,3-a][1,4]diazepin-2-yl]propionic acid, 3-[4-(2-methylphenyl)-6,9-dimethyl-6H-thieno[3,3-f][1,2,4]triazolo-[4,3-a][1,4]diazepin-2-yl]propionic acid, 4-[4-(2-chlorophenyl)-6,9-dimethyl-6H-thieno[3,2-f][1,2,4]triazolo[4,3-a][1,4]diazepin-2-yl]butyric acid, 5-[4-(2-chlorophenyl)-6,9-dimethyl-6H-thieno[3,2-f][1,2,4]triazolo[4,3-a][1,4]diazepin-2-yl]valeric acid, 3-[4-(2-chlorophenyl)-9-ethyl-6-methyl-6H-thieno[3,2-f][1,2,4]triazolo[4,3-a][1,4]diazepin-2-yl]propionic acid, 2-[4-(2-chlorophenyl)-9-ethyl-6-methyl-6H-thieno[3,2-f][1,2,4]triazolo[4,3-a][1,4]diazepin-2-yl]acetic acid.

EXAMPLE 7

To a solution of 1.4 g of 3-[4-(2-chlorophenyl)-6,9-dimethyl-6H-thieno[3,2-f][1,2,4]triazolo[4,3-a][1,4]diazepin-2-yl]propionic acid in 20 ml of dimethylformamide are added 0.5 g of N-hydroxybenzotriazole and 0.35 g of morpholine and stirred at room temperature for 10 minutes. To the mixture is added 0.9 g of dicyclohexyl carbodiimide under ice-cooling and stirred for 3 hours and furthermore stirred at room temperature for 18 hours. The resulting dicyclohexylurea is filtered off, the filtrate is concentrated under reduced pressure and then the residue is dissolved in 100 ml of chloroform. The solution is washed with 50 ml of 5% aqueous sodium hydrogencarbonate solution and water and dried over anhydrous magnesium sulfate. After separating by filtration, the filtrate is concentrated under reduced pressure and the residue is crystallized from isopropyl ether. The precipitated crystals are collected by filtration and recrystallized from ethyl acetate to give 1 g of 3-[4-(2-chlorophenyl)-6,9-dimethyl-6H-thieno[3,2-f][1,2,4]triazolo[4,3-a][1,4]diazepin-2-yl]propionic acid morpholide as colorless crystals, melting at 162°–163° C.

EXAMPLE 8

To a solution of 1.1 g of 3-[4-(2-chlorophenyl)-6,9-dimethyl-6H-thieno[3,2-f][1,2,4]triazolo[4,3- a][1,4]diazepin-2-yl]propionic acid in 15 ml of dimethylformamide are added 0.4 g of N-hydroxybenzotriazole and 0.25 g of piperidine and stirred at room temperature for 10 minutes. To the mixture is added 0.65 g of dicyclohexyl carbodiimide under ice-cooling and stirred for 1 hour and furthermore stirred at room temperature for 20 hours. The resulting dicyclohexylurea is filtered off and to the filtrate is added 50 ml of chloroform. The solution is washed with 5% aqueous sodium hydrogencarbonate solution and water and dried over anhydrous magnesium sulfate. After separating by filtration, the filtrate is concentrated under reduced pressure and the residue is crystallized from ethyl acetate. The precipitated crystals are collected by filtration and recrystallized from ethyl acetate to give 0.9 g of 3-[4-(2-chlorophenyl)-6,9-dimethyl-6H-thieno[3,2-f][1,2,4]triazolo[4,3-a][1,4]diazepin-2-yl]propionic acid piperidide as colorless crystals, melting at 157°-160° C.

EXAMPLE 9

To a solution of 1.1 g of 3-[4-(2-chlorophenyl)-6,9-dimethyl-6H-thieno[3,2-f][1,2,4]triazolo[4,3-a][1,4]diazepin-2-yl]propionic acid in 15 ml of dimethylformamide are added 0.4 g of N-hydroxybenzotriazole and 0.4 ml of dipropylamine and stirred at room temperature for 10 minutes. To the mixture is added 0.65 g of dicyclohexyl carbodiimide under ice-cooling and stirred for 4 hours and furthermore stirred at room temperature for 16 hours. The resulting dicyclohexylurea is filtered off and to the filtrate is added 50 ml of chloroform. The solution is washed with 5% aqueous sodium hydrogencarbonate solution and water and dried over anhydrous magnesium sulfate. After separating by filtration, the filtrate is concentrated under reduced pressure and the residue is subjected to chromatography on silica gel and then eluted with a mixture of chloroform-methanol (100:1 to 100:3). The eluate of the objective fraction is concentrated under reduced pressure to give 1 g of 3-[4-(2-chlorophenyl)-6,9-dimethyl-6H-thieno[3,2-f][1,2,4]triazolo[4,3-a][1,4]diazepin-2-yl]propionic acid N,N-dipropylamide as pale yellow viscous oil.

EXAMPLE 10

To a solution of 1.1 g of 2-[4-(2-chlorophenyl)-6,9-dimethyl-6H-thieno[3,2-f][1,2,4]triazolo[4,3-a][1,4]diazepin-2-yl]acetic acid in 15 ml of dimethylformamide are added 0.4 g of N-hydroxybenzotriazole and 0.27 ml of morpholine and stirred at room temperature for 10 minutes. To the mixture is added 0.65 g of dicyclohexyl carbodiimide under ice-cooling and stirred for 1 hour and furthermore stirred at room temperature for 18 hours. The resulting dicyclohexylurea is filtered off and to the filtrate is added 50 ml of chloroform. The solution is washed with 5% aqueous sodium hydrogen-carbonate carbonate solution and water and dried over anhydrous magnesium sulfate. After separating by filtration, the filtrate is concentrated under reduced pressure and the residue is crystallized from isopropyl ether. The precipitated crystals are collected by filtration and recrystallized from ethyl acetate to give 0.9 g of 2-[4-(2-chlorophenyl)-6,9-dimethyl-6H-thieno[3,2-f][1,2,4]triazolo[4,3-a][1,4]diazepin-2-yl]acetic acid morpholide as colorless crystals, melting at 126°-129° C.

EXAMPLE 11

To a solution of 1.1 g of 2-[4-(2-chlorophenyl)-6,9-dimethyl-6H-thieno[3,2-f][1,2,4]triazolo[4,3-a][1,4]diazepin-2-yl]acetic acid in 15 ml of dimethylformamide are added 0.4 g of N-hydroxybenzotriazole and 0.3 g of piperidine and stirred at room temperature for 10 minutes. To the mixture is added 0.65 g of dicyclohexyl carbodiimide under ice-cooling and stirred for 1 hour and furthermore stirred at room temperature for 21 hours. The resulting dicyclohexylurea is filtered off and to the filtrate is added 100 ml of chloroform. The solution is washed with 5% aqueous sodium hydrogencarbonate solution and water and dried over anhydrous magnesium sulfate. After separating by filtration, the filtrate is concentrated under reduced pressure and the residue is crystallized from isopropyl ether. The precipitated crystals are collected by filtration and recrystallized from ethyl acetate to give 0.9 g of 2-[4-(2-chlorophenyl)-6,9-dimethyl-6H-thieno[3,2-f][1,2,4]triazolo[4,3-a][1,4]diazepin-2-yl]acetic acid piperidide as colorless crystals, melting at 182°-183° C.

EXAMPLE 12

To a solution of 1 g of 3-[4-(2-chlorophenyl)-6-ethyl-9-methyl-6H-thieno[3,2-f][1,2,4]triazolo[4,3-a][1,4]diazepin-2-yl]propionic acid in 15 ml of dimethylformamide are added 0.4 g of N-hydroxybenzotriazole and 0.23 ml of morpholine and stirred at room temperature for 10 minutes. To the mixture is added 0.6 g of dicyclohexyl carbodiimide under ice-cooling and stirred for 1 hour and furthermore stirred at room temperature for 18 hours. The resulting dicyclohexylurea is filtered off and to the filtrate is added 100 ml of chloroform. The solution is washed with 5% aqueous sodium hydrogencarbonate solution and water and dried over anhydrous magnesium sulfate. After separating by filtration, the filtrate is concentrated under reduced pressure and the residue is crystallized from isopropyl ether. The precipitated crystals are collected by filtration and recrystallized from a mixture of isopropyl ether-ethyl acetate (1:1) to give 0.8 g of 3-[4-(2-chlorophenyl)-6-ethyl-9-methyl-6H-thieno[3,2-f][1,2,4]triazolo-[4,3-a][1,4]diazepin-2-yl]propionic acid morpholide as colorless crystals, melting at 145°-147° C.

The following compounds can be prepared in similar manners as the above Examples

(13) 2-[4-(2-chlorophenyl)-6-ethyl-9-methyl-6H-thieno[3,2-f][1,2,4]triazolo[4,3-a][1,4]diazepin-2-yl]acetic acid morpholide, melting at 178°-180° C.

(14) 4-[4-(2-chlorophenyl)-6,9-dimethyl-6H-thieno[3,2-f][1,2,4]triazolo[4,3-a][1,4]diazepin-2-yl]butyric acid amide, melting at 118°-121° C.

(15) 3-[4-(2-chlorophenyl)-6-ethyl-9-methyl-6H-thieno[3,2-f][1,2,4]triazolo[4,3-a][1,4]diazepin-2-yl]propionic acid piperidide, melting at 171°-173° C.

(16) 3-[4-(2-chlorophenyl)-6,9-dimethyl-6H-thieno[3,2-f][1,2,4]triazolo[4,3-a][1,4]diazepin-2-yl]propionic acid 4-isobutyl-1-piperazide, as white amorphous

(17) 5-[4-(2-chlorophenyl)-6,9-dimethyl-6H-thieno[3,2-f][1,2,4]triazolo[4,3-a][1,4]diazepin-2-yl]valeric acid amide, as white amorphous

(18) 4-[4-(2-chlorophenyl)-6,9-dimethyl-6H-thieno[3,2-f][1,2,4]triazolo[4,3-a][1,4]diazepin-2-yl]butyric acid piperidide, as white amorphous

(19) 5-[4-(2-chlorophenyl)-6,9-dimethyl-6H-thieno[3,2-f][1,2,4]triazolo[4,3-a][1,4]diazepin-2-yl]valeric acid piperidide, as white amorphous

(20) 5-(2-chlorophenyl)-3,4-dihydro-7,10-dimethyl-3-morpholinocarbonyl-2H,7H-cyclopenta[4,5]-thieno[3,2-f][1,2,4]triazolo[4,3-a][1,4]diazepine, $^1$H-NMR(CDCl$_3$) δppm: 7.3–7.6 (4H, m), 4.22–4.44 (1H, q), 2.64 (3H, s), 2.05 (3H, d), 2.00–4.00 (m, 13H), MS(z/m) 481

(21) 5-(2-chlorophenyl)-3,4-dihydro-7,10-dimethyl-3-thiomorpholinocarbonyl-2H,7H-cyclopenta[4,5]-thieno[3,2-f][1,2,4]triazolo[4,3-a][1,4]diazepine, $^1$H-NMR(CDCl$_3$) δppm: 7.3–7.6 (4H, m), 4.20–4.44 (1H, q), 2.64 (3H, s), 2.06 (3H, d), 2.00–4.00 (m, 13H), MS(z/m) 497

(22) 5-(2-chlorophenyl)-3,4-dihydro-7,10-dimethyl-3-(1-pyrroridinylcarbonyl)-2H,7H-cyclopenta[4,5]-thieno[3,2-f][1,2,4]triazolo[4,3-a][1,4]diazepine, $^1$H-NMR(CDCl$_3$) δppm: 7.2–7.4 (4H, m), 4.20–4.44 (1H, q), 2.64 (3H, s), 2.06 (3H, d), 1.8–4.0 (m, 13H), MS(z/m) 465

(23) 5-(2-chlorophenyl)-3,4-dihydro-7,10-dimethyl-3-(4-methyl-1-piperazinylcarbonyl)-2H,7H-cyclopenta[4,5]thieno[3,2-f][1,2,4]triazolo[4,3-a][1,4]diazepine, $^1$H-NMR(CDCl$_3$) δppm: 7.2–7.4 (4H, m), 4.2–4.4 (1H, q), 2.64 (3H, s), 2.30 (3H, s), 2.05 (3H, d), 2.0–4.0 (13H, m), MS(z/m) 494

(24) 6-(2-chlorophenyl)-2,3,4,5-tetrahydro-8,11-dimethyl-3-morpholinocarbonyl-8-(1)benzothieno[3,2-f][1,2,4]triazolo[4,3-a][1,4]diazepine, melting at 232°–238° C.

Pharmaceutical preparations (1) Tablets

A composition of 0.5 part of the compound of Example 1, 25 parts of lactose, 35 parts of crystalline cellulose and 3 parts of corn starch is mixed well, and kneaded with binder prepared by 2 parts of corn starch. The paste is passed through a 16 mesh sieve and dried in an oven at 50° C., and forced through a 24 mesh sieve. The powder thus obtained, 8 parts of corn starch, 11 parts of crystalline cellulose and 9 parts of talc are mixed well and the mixture was compressed with a punch into tablets containing 0.5 mg of active ingredient.

(2) 1% Powder

A composition of 1 part of the compound of Example 1 and 90 parts of lactose is mixed well and kneaded with binder prepared by a suitable amount of methylcellulose. The mixture was passed through a 16 mesh sieve and dried in an oven at 50° C. The dried granules were forced through 32 mesh sieve with pressure and mixed with a suitable amount of silicon dioxide to produce 1% powder.

Although the present invention has been adequately discussed in the foregoing specification and examples included therein, one readily recognizes that various changes and modifications may be made without departing from the spirit and scope of the present invention.

We claim:

1. A thienotriazolodiazepine compound of the formula:

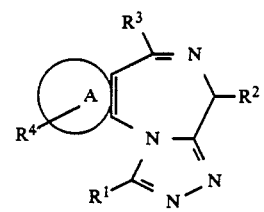

or a pharmaceutically acceptable salt thereof, wherein
R$^1$ is alkyl;
R$^2$ is methyl or trifluoromethyl;
R$^3$ is phenyl or phenyl substituted by one substituent selected from the group consisting of halogen, alkyl and alkoxy;
R$^4$ is —B$_l$R$^5$
In the formula —B$_l$R$^5$, when l>0, R$^5$ is hydroxy; halogen; a group represented by —N(R$^{11}$)(R$^{12}$), wherein R$^{11}$ and R$^{12}$ are the same or different and each is hydrogen; straight or branched chain alkyl having 1 to 10 carbon atoms, which may be substituted by amino, alkylamino, dialkylamino or cyclic amino; or R$^{11}$ and R$^{12}$ together with the adjacent nitrogen atom form a saturated 5- to 7-membered heterocycle selected from the group consisting of 1-pyrrolidinyl, piperidino, 1-piperazinyl, 1-perhydroazepinyl, morpholino, thiomorpholino, 4-methyl-1-piperazinyl and 2,6-dimethylmorpholino; arylsulfonyloxy which may be mono- or poly-substituted by straight or branched chain alkyl and/or alkoxy having 1 to 4 carbon atoms; straight or branched chain alkylsulfonyloxy having 1 to 4 carbon atoms; or straight or branched chain alkylcarbonyloxy having 2 to 12 carbon atoms; and when l≧0, R$^5$ is —COOH; cyano; straight or branched chain alkoxycarbonyl having 1 to 4 carbon atoms; or a group represented by (R$^{17}$)(R$^{18}$)NCO—, wherein R$^{17}$ and R$^{18}$ are the same or different and each is hydrogen, phenyl, substituted phenyl, aralkyl or straight or branched chain alkyl, alkenyl or alkynyl having 1 to 10 carbon atoms, or R$^{17}$ and R$^{18}$ together with the adjacent nitrogen atom form a 5- to 7-membered heterocycle selected from the group consisting of 1-pyrrolidinyl, piperidino, 1-piperazinyl, 1-perhydroazepinyl, morpholino, thiomorpholino, 4-methyl-1-piperazinyl, 4-isobutyl-1-piperazinyl and 3-thiazolidinyl; B is straight or branched chain alkylene having 1 carbon atoms, which may be di-substituted by R$^5$, wherein R$^5$ is the same or different; and l is 0, 1, 2, 3, 4, 5, 6, 7, 8, 9 or 10, and
ring A is thiophene ring, tetrahydrobenzothiophene ring or 4,5-dihydro-6H-cyclopenta[b]thiophene ring.

2. A compound of claim 1 selected from the group consisting of
3-[4-(2-chlorophenyl)-6,9-dimethyl-6H-thieno[3,2-f][1,2,4]triazolo[4,3-a][1,4]diazepin-2-yl]propionic acid morpholide,
5-(2-chlorophenyl)-3,4-dihydro-7,10-dimethyl-3-morpholinocarbonyl-2H,7H-cyclopenta[4,5]thieno[3,2-f][1,2,4]triazolo[4,3-a][1,4]diazepine,
5-(2-chlorophenyl)-3,4-dihydro-7,10-dimethyl-3-morpholinomethyl-2H,7H-cyclopenta[4,5]thieno[3,2-f][1,2,4]triazolo[4,3-a][1,4]diazepine, 5-(2-chlorophenyl)-3,4-dihydro-7,10-dimethyl-3-thiomorpholinocarbonyl-2H,7H-cyclopenta[4,5]-thieno[3,2-f][1,2,4]triazolo-[4,3-a][1,4]diazepine, 6-(2-chlorophenyl)-2,3,4,5-tetrahydro-8,11-dimethyl-3-morpholinocarbonyl-8-(1)benzothieno[3,2-f][1,2,4]triazolo[4,3-a][1,4]diazepine, 3-[4-(2-chlorophenyl)-6,9-dimethyl-6H-thieno[3,2-f][1,2,4]triazolo[4,3-a][1,4]diazepin-2-yl]propionic acid 4-isobutyl-1-piperazide, 3-[4-(2-chlorophenyl)-6,9-dimethyl-6H-thieno[3,2-f][1,2,4]triazolo[4,3-a][1,4]diazepin-2-yl]propionic acid N,N-dipropylamide, 3-[4-(2-chlorophenyl)-6,9-dimethyl-6H-thieno[3,2-f][1,2,4]triazolo[4,3-a][1,4]diazepin-2-yl]propionic acid piperidide, 4-(2-chlorophenyl)-6,9-dimethyl-2-(6-morpholinohexyl)-6H-thieno[3,2-f][1,2,4]triazolo[4,3-a][1,4]diazepine and 4-(2-chlorophenyl)-6,9-dimethyl-2-(3-morpholinopropyl)-6H-thieno[3,2-f][1,2,4]triazolo[4,3-a][1,4]diazepine, or a pharmaceutically acceptable acid addition salt thereof.

3. A pharmaceutical composition for the prevention or treatment of various PAF-induced diseases comprising a therapeutically effective amount of the compound of claim 1, and a pharmaceutically acceptable additive.

* * * * *